United States Patent [19]
Pittet

[11] Patent Number: 4,716,249
[45] Date of Patent: * Dec. 29, 1987

[54] PROCESS FOR PREPARING NATURAL BENZALDEHYDE AND ACETALDEHYDE

[75] Inventor: Alan O. Pittet, Atlantic Highlands, N.J.

[73] Assignee: International Flavors & Fragrances Inc., New York, N.Y.

[*] Notice: The portion of the term of this patent subsequent to Oct. 14, 2003 has been disclaimed.

[21] Appl. No.: 925,788

[22] Filed: Oct. 31, 1986

Related U.S. Application Data

[60] Continuation of Ser. No. 872,913, Jun. 11, 1986, which is a division of Ser. No. 780,298, Sep. 26, 1985, Pat. No. 4,617,419.

[51] Int. Cl.$^4$ .............................................. C07C 45/51
[52] U.S. Cl. ..................................... 568/433; 568/458; 568/464; 568/463
[58] Field of Search ............... 568/464, 461, 463, 458, 568/433

[56] References Cited

U.S. PATENT DOCUMENTS

| | | | |
|---|---|---|---|
| 1,416,128 | 5/1922 | Scott et al. | 424/44 |
| 4,617,419 | 10/1986 | Wiener et al. | 568/464 |
| 4,673,766 | 6/1987 | Buck et al. | 568/433 |

OTHER PUBLICATIONS

Guthrie et al., "Canadian J. Chem.", vol. 62 (1984), pp. 1441-1445.
Reeves et al., "TAPPI", vol. 48, No. 2 (1965), pp. 121-125.
Bedoukin, "Perfumery & Flavoring Synthesis" (1967), Elsevier Pub. Co., N.Y. (1967), pp. 91, 92 and 97.

Primary Examiner—Werren B. Lone
Attorney, Agent, or Firm—Arthur L. Liberman

[57] ABSTRACT

Described is a process for preparing natural benzaldehyde and acetaldehyde and compositions of matter containing natural benzaldehyde and acetaldehyde as well as products produced thereby and organoleptic utilities thereof, which process comprises the step of contacting with base naturally occurring cinnamaldehyde or a natural product rich in cinnamaldehyde such as Ceylon oil of cinnamon, Ceylon cinnamon bark, Saigon cinnamon bark, cassia oil, Ceylon cinnamon quills, cinnamon leaf oil, oil of cinnamon Madagascar or the like according to the reaction:

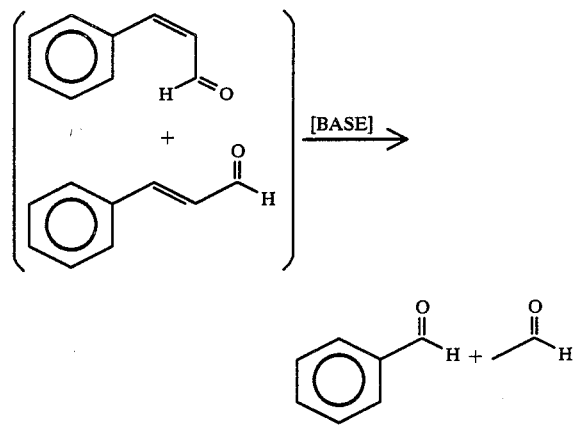

the reaction taking place in the absence of any other reagents except inert solvent and ionic surfactant or emulsifier.

1 Claim, 15 Drawing Figures

GC-IR SPECTRUM FOR EXAMPLE I.

GC-IR SPECTRUM FOR EXAMPLE I.

GC-IR SPECTRUM FOR EXAMPLE II.

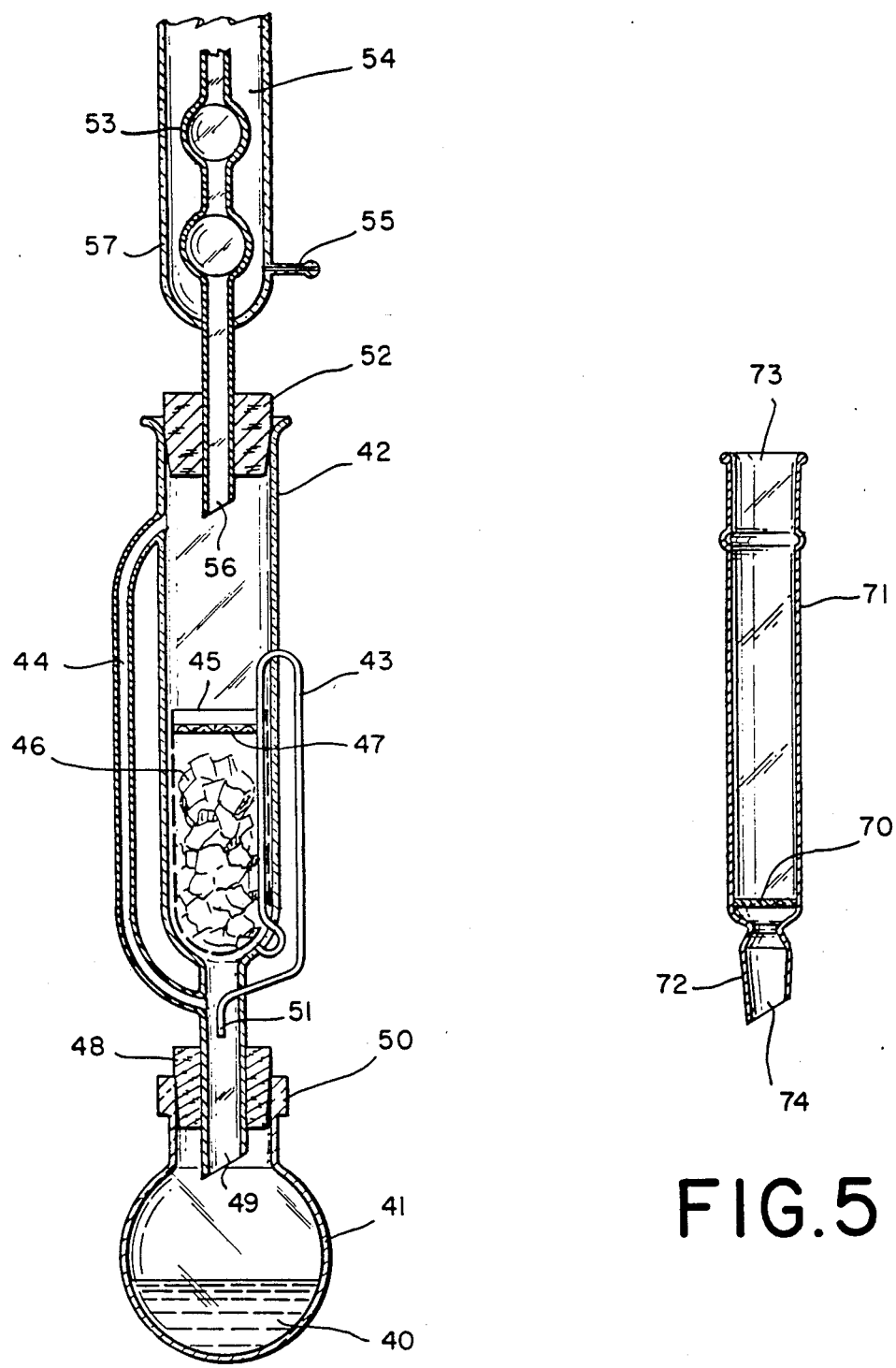

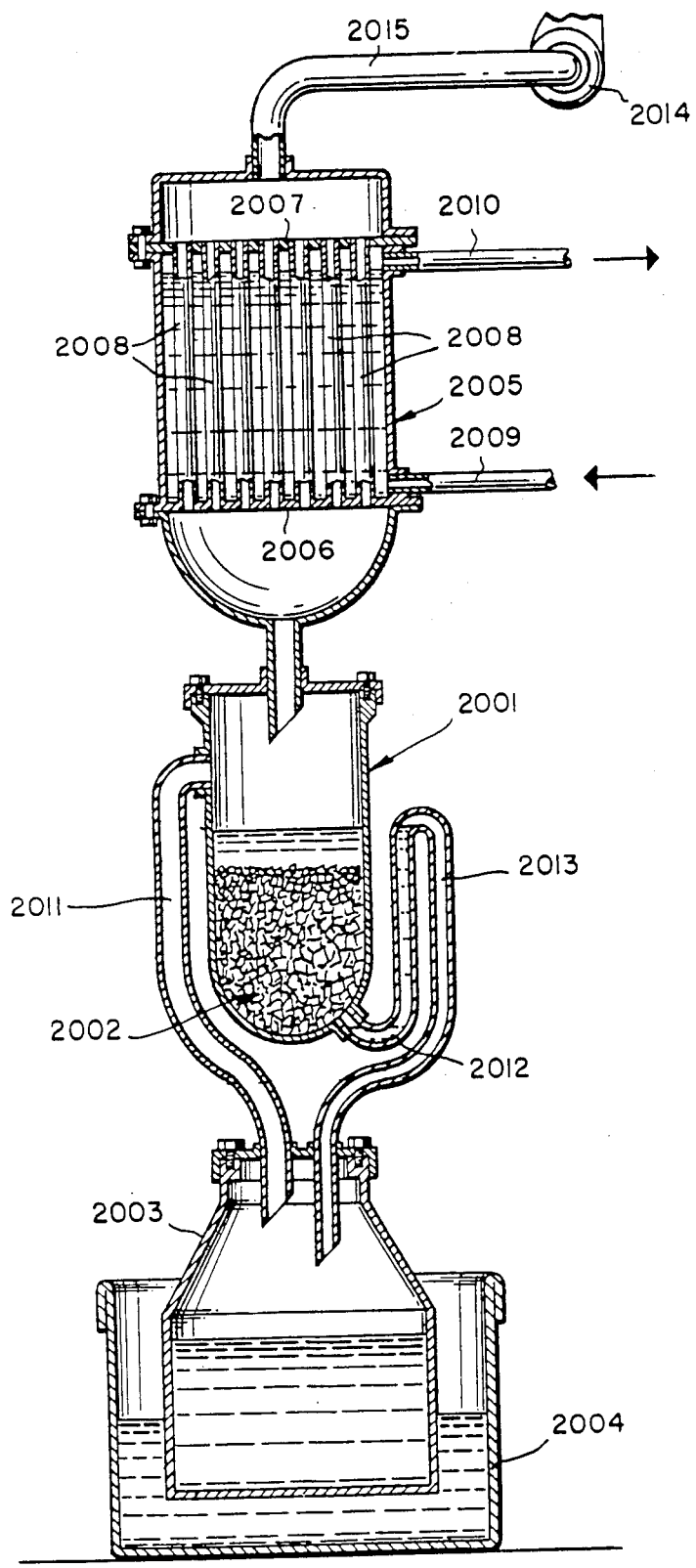

111

GLC PROFILE FOR EXAMPLE VI.

101

GLC PROFILE FOR EXAMPLE VI.

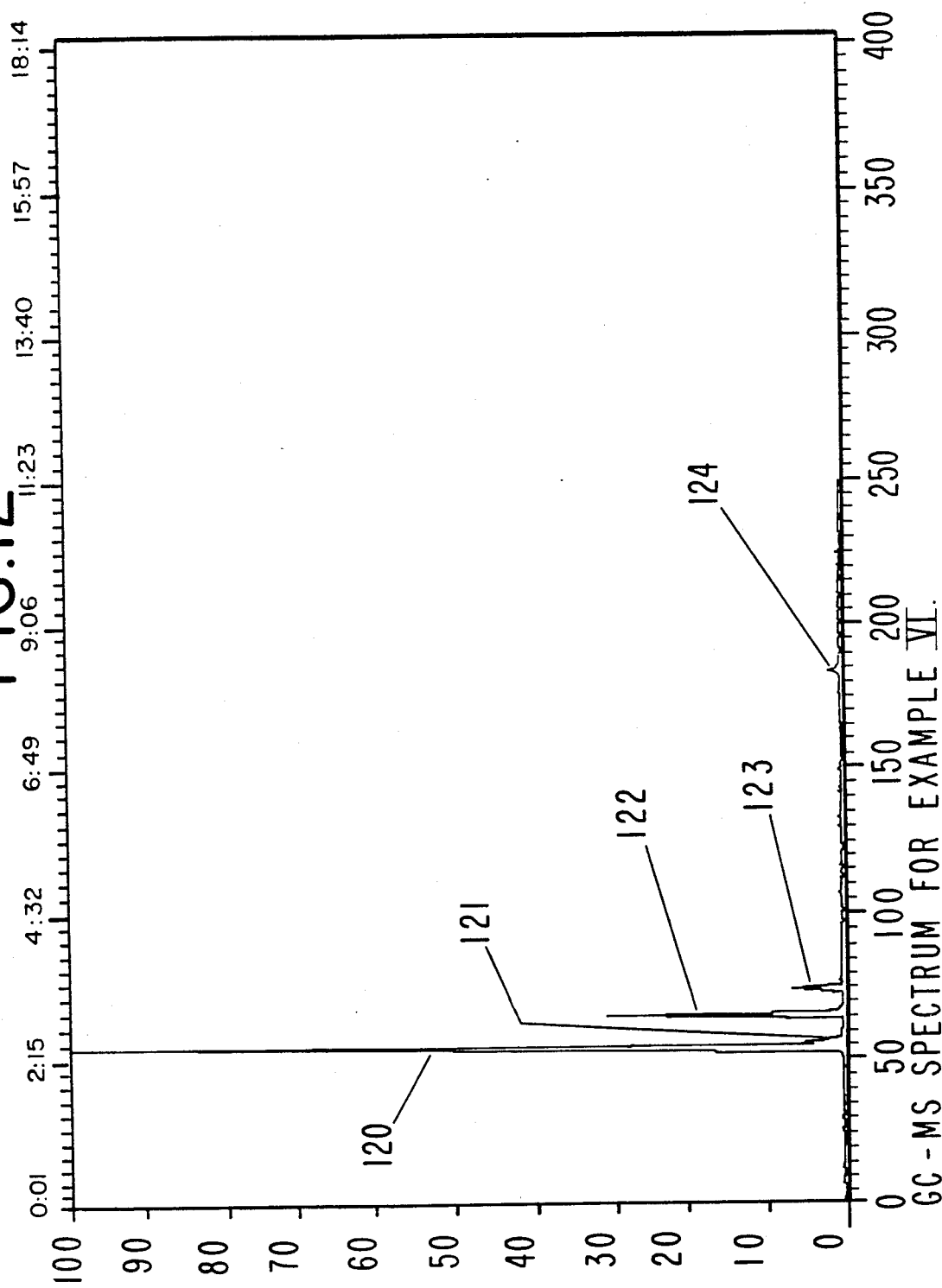
FIG. 12  GC-MS SPECTRUM FOR EXAMPLE VI.

PROCESS FOR PREPARING NATURAL BENZALDEHYDE AND ACETALDEHYDE

This application is a continuation-in-part of application for U.S. Letters Patent, Ser. No. 872,913 filed on June 11, 1986, which, in turn, is a divisional of application for U.S. Letters Patent, Ser. No. 780,298 filed on Sept. 26, 1985, now U.S. Pat. No. 4,617,419 issued on Oct. 14, 1986.

BACKGROUND OF THE INVENTION

A major use of natural benzaldehyde is an ingredient in "natural" cherry flavor and other flavors for augmenting or enhancing the aroma or taste of consumable materials including foodstuffs, chewing gums, medicinal products, toothpastes, chewing tobacco, smoking tobacco and smoking tobacco articles.

A major use of natural acetaldehyde is an ingredient in "natural" orange flavor and other flavors for augmenting or enhancing the aroma or taste of consumable materials including foodstuffs, chewing gums, medicinal products, toothpastes and chewing tobacco.

Natural benzaldehyde has been used in natural cherry flavors in the form of apricot kernel extract as is taught in U.S. Pat. No. 1,416,128 issued on May 16, 1922. An undesirable feature of the known processes for preparing natural benzaldehyde from apricot kernels or re-ground press cake is that along with the benzaldehyde, toxic hydrocyanic acid is produced which must be separated completely from the benzaldehyde and from the rest of the oil prior to use. Other techniques for producing natural benzaldehyde are known but these techniques produce it in such yields as to cause the resulting process to be uneconomical. For example, Hockenhull, et al, Biochem. J., 50, 605–9, (1952) (Title: "Oxidation of Phenylacetic Acid by Penicillium chrysogenum" discloses production of benzaldehyde starting with phenylacetic acid through either benzyl alcohol or mandelic acid via the sequences:

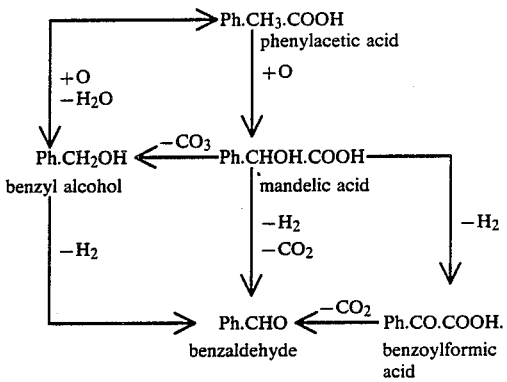

Towers, et al, Can. J. Zool. 1972, 50(7), 1047–50 ("Defensive secretion: biosynthesis of hydrogen cyanide and benzaldehyde from phenylalanine by a millipede") discloses a biosynthetic pathway for the production of benzaldehyde from dietary phenylalanine in "Oxidus gracilis, thusly:

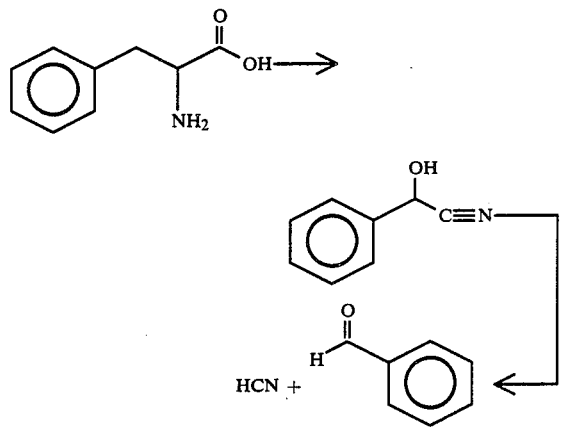

Halpin, et al, Biochemistry, 1981, Volume 20, pages 1525–1533 (Title: "Carbon-13 Nuclear Magnetic Resonance Studies of Mandelate Metabolism in Whole Bacterial Cells and in Isolated, in Vivo Cross-Linked Enzyme Complexes") discloses the biochemical pathway from mandelate ion to benzaldehyde thusly:

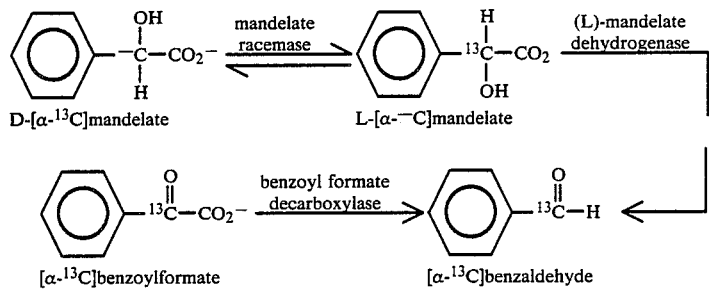

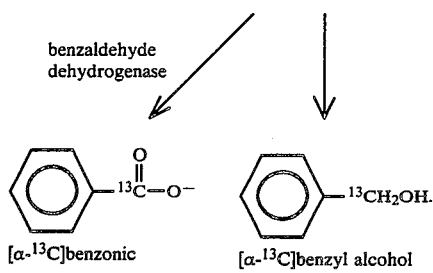

[α-$^{13}$C]benzonic    [α-$^{13}$C]benzyl alcohol

Reeves, et al, TAPPI 48(2), pages 121–5, (1965) (Title: "Reaction Products Formed Upon the Alkaline Peroxide Oxidation of Lignin-Related Model Compounds") discloses the effect of alkaline hydrogen peroxide oxidation on cinnamaldehyde whereby the cinnamaldehyde is split at the double bond with the formation of the corresponding benzaldehyde and benzoic acid according to the reaction:

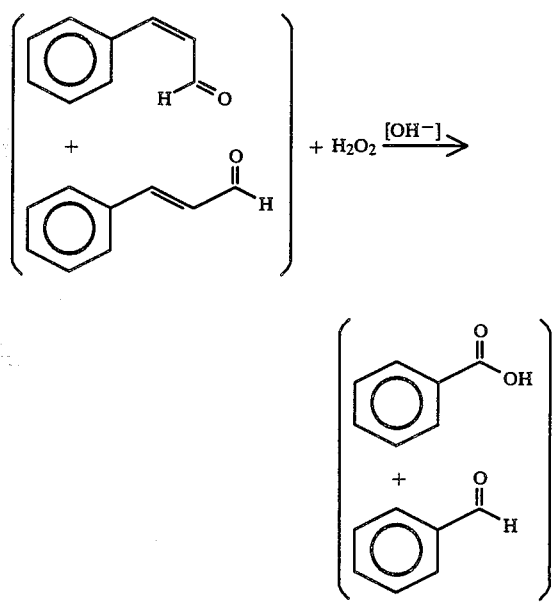

At page 124, column 1, paragraph 1, Reeves. et al theorizes that a "reverse aldol reaction is not responsible for the formation of vertraldehyde due to the fact that acetaldehyde the other product of the potential "reverse aldol reaction" was not obtained. Therefore, my discovery of the "retro-aldol" reaction taking place, to wit:

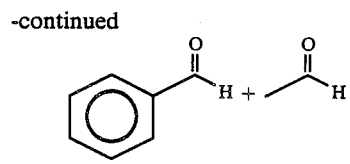

was unexpected and unobvious. The "retro-aldol" reaction, to wit:

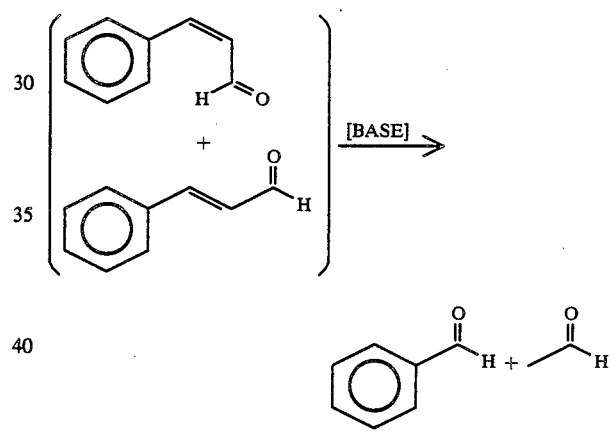

indeed, took place due to the different reaction conditions from those proposed and set forth in Reeves, et al; different insofar as temperature of reaction and time of reaction are concerned, longer times of reaction and higher temperatures of reaction being the conditions in my "retro-aldol" reaction as opposed to shorter times of reaction and lower temperatures insofar as the Reeves, et al reaction is concerned.

In my own invention no reagents other than base and naturally occurring cinnamaldehyde and solvent and ionic surfactant or emulsifier are utilized to carry out the "retro-aldol" reaction of my invention, to wit:

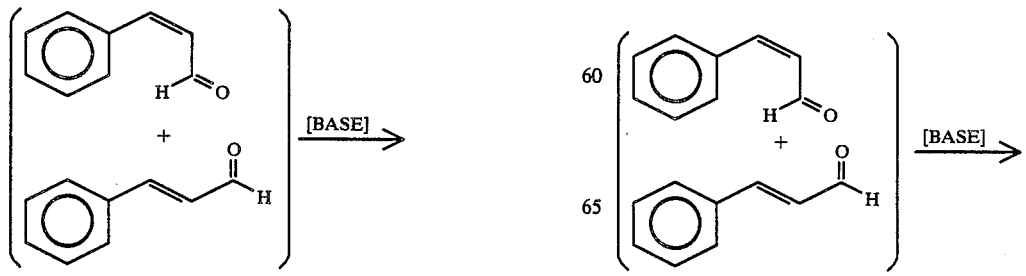

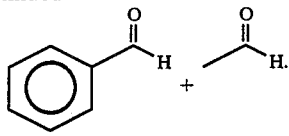

The process of my invention thus gives rise to unobvious, unexpected and advantageous results and represents an advance in the art in the production of "natural" benzaldehyde taken alone or in combination with natural cinnamaldehyde; and, further, in the production of "natural acetaldehyde".

SUMMARY OF THE INVENTION

My invention is directed to the production of "natural" benzaldehyde and/or "natural" acetaldehyde taken alone or in admixture with "natural" cinnamaldehyde according to a reaction where "natural" cinnamaldehyde is subject to a "retro-aldol" reaction, thusly:

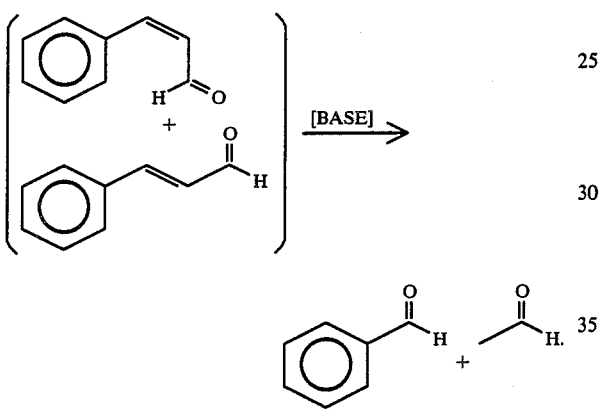

The cinnamaldehyde reactant may occur in either the "cis" form having the structure:

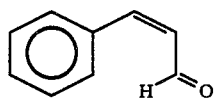

and/or the "trans" form having the structure:

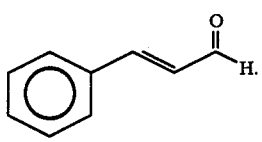

The cinnamaldehyde may be in recovered form from natural sources as by distillation or extraction or the cinnamaldehyde may exist in its natural state immediately prior to the reaction, thusly:

(I) Oil of Cinnamon Ceylon;
(II) Ceylon Cinnamon Bark (*Cinnamomum zeylanicum* Nees ex Blume (fam. Lauraceae));
(III) The bark of Saigon Cinnamon (*Cinnamomum loureirii* Nees (fam. Lauraceae);
(IV) The bark of Cassia cinnamon (ex *Cinnamomum cassia* (Nees)) Nees ex Blume (fam. Lauraceae);
(V) The bark of Saigon cinnamon;
(VI) Oil of Cinnamon Bark Ceylon;
(VII) "Quills" from Ceylon cinnamon (including "fines", "Barcelona" and "Hamburg");
(VIII) Ceylon cinnamon quillings and featherings;
(IX) Ceylon cinnamon chips;
(X) Ceylon cinnamon bark oil;
(XI) Oil of cinnamon Seychelles;
(XII) Oil of cinnamon Madagascar;
(XIII) Leaves of Cassia;
(XIV) Cassia Bark (*Cassia lignea* in ground or powdered form);
(XV) Oil of Cassia.

Thus, the cinnamaldehyde source may be treated with base such as sodium bicarbonate, potassium bicarbonate, sodium carbonate, potassium carbonate, lithium carbonate, lithium bicarbonate, magnesium hydroxide, calcium hydroxide, calcium carbonate, proline having the structure:

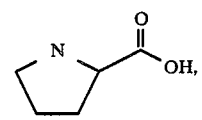

choline having the structure:

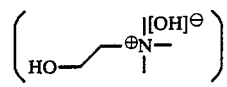

or a natural choline source such as natural lecithin having the structure:

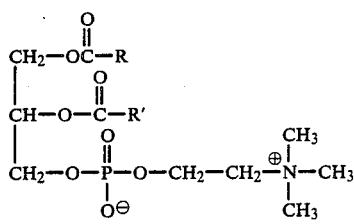

in the presence of base (wherein the residues:

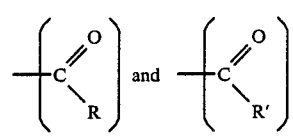

represent palmitoyl, stearoyl, oleyl, linoleyl, linolenyl and $C_{20}$ to $C_{22}$ acid residues) [examples of naturally occurring lecithin are soybean lecithin (reference: "Soybeans, Volume II, (Interscience Publishing Company, New York, 1951), pages 593–647 and natural phosphatide lecithin] whereby a "retro-aldol" reaction takes place, thusly:

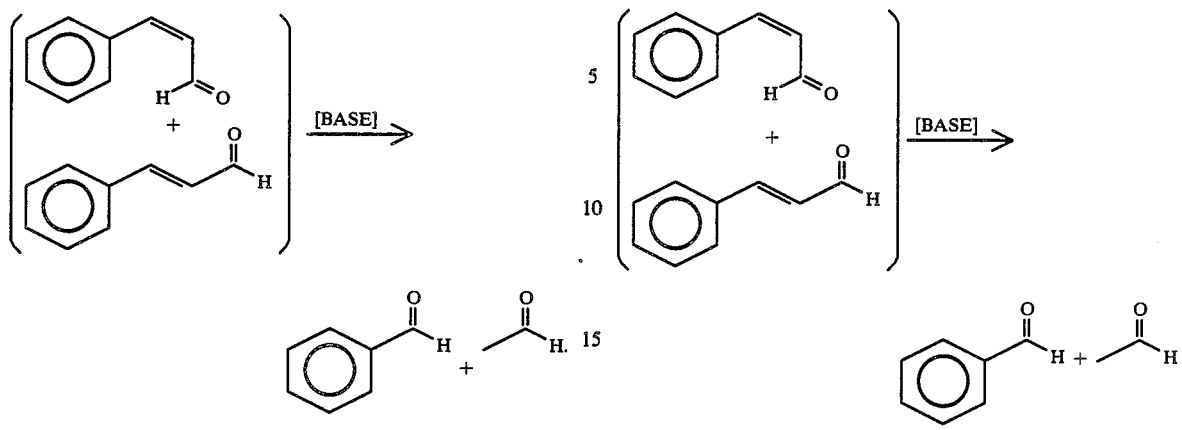

Lecithin according to the "The Merck Index", Tenth Edition, Published by Merck & Company, Inc. of Rahway, N.J., 1983, at Monograph 5271 indicates that lecithins use is:

"edible and digestible surfactant and emulsifier of natural origin . . . "

The reference "The Merck Index", Tenth Edition, 1983 is incorporated by reference herein.

A requirement of my invention is that no other reagents be present which would cause the reaction to give rise to a composition containing benzaldehyde or acetaldehyde which cannot be described as "natural". Thus the use of substances such as hydrogen peroxide and/or sodium hydroxide in the reaction mass would give rise to a material not contemplated within the scope of my invention.

Thus, my invention specifically is intended to exclude processes such as those of the prior art, for example, Reeves, et al, TAPPI, 48(2), 121–5, (1965) which discloses the reaction:

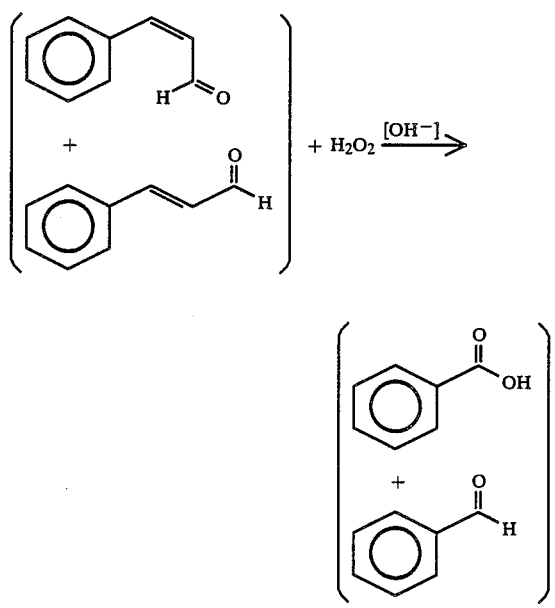

The reaction of my invention, to wit: may be carried out in a standard reaction vessel at reflux conditions (preferably when the cinnamaldehyde-bearing reactant is in the liquid phase, e.g., cinnamon oil or cassia oil); or it may be carried out in solid-liquid phase reaction equipment, e.g., "Soxhlet"-type equipment (preferably when the cinnamaldehyde-bearing reactant is in the solid phase). Thus, the reaction of my invention may be carried out in a "Soxhlet" extraction vessel with the actual reaction taking place in the "Soxhlet" thimble as more specifically described, infra, or the reaction of my invention may be carried out in a "Soxhlet" extraction vessel with the actual reaction taking place in the reboiler flask or vessel. The case where the reaction takes place in the "Soxhlet" thimble occurs when, for example, pulverized cinnamaon bark of one of the above types is intimately admixed with lime or magnesium hydroxide or the like and the resulting solid mixture is placed in the "Soxhlet" thimble.

In either case, the reaction may take place in the presence of (i) $C_1$–$C_5$ alcohols, (ii) water, or (iii) aqueous mixtures of $C_1$–$C_5$ alcohols and water. Examples of $C_1$–$C_5$ alcohols are methanol, ethyl alcohol, isopropyl alcohol, n-propyl alcohol, n-butanol, secondary butanol, tertiary butanol, n-amyl alcohol, t-amyl alcohol and isobutanol. The weight ratio of alcohol:water when an alcoholic solution is used, may vary, and is preferably from about 6 parts alcohol: 4 parts water (by weight) up to about 1 part alcohol: about 10 parts water (by weight).

The reaction is carried out at temperatures such that acetaldehyde and benzaldehyde are removed from the reaction mass as they are formed thereby favoring the "retro-aldol" reaction. Hence, temperatures substantially greater than the boiling point of acetaldehyde are to be used. The boiling point of acetaldehyde is 21° C. at atmospheric pressure. Pressures of from about 0.2 atmospheres up to about 10 atmospheres may be used in carrying out this reaction. Thus, for example, refluxing water at 1 atmosphere gives rise to a reaction temperature of about 90° C. whereas refluxing 50:50 ethanol:water at atmospheric pressure gives rise to a reaction temperature of about 80° C. The reaction temperature may thus vary from about 40° C. up to about 150° C. The reaction pressure may thus vary from about 0.2 atmospheres up to about 10 atmospheres. The reaction time may vary from about 5 hours up to about 80 hours. The longer the reaction time, the greater the degree of "completion" of the reaction (giving rise to a greater ratio of benzaldehyde:cinnamaldehyde in the final product). The shorter the period of rection time the higher the temperature required in order to substantially "complete" the reaction (whereby the weight percent of benzaldehyde in the reaction mass is greater than about 40%).

Thus, within the meaning of my specification, the term "completion" of reaction means the formation in the reaction mass of at least a 10% yield of "natural" benzaldehyde and a 10% yield of acetaldehyde up to about a 95% yield of "natural" benzaldehyde and a 95% yield of "natural" acetaldehyde. Carrying out my process in order to yield less than 10% of benzaldehyde or acetaldehyde or greater than 95% yield of benzaldehyde or acetaldehyde becomes uneconomical and is not contemplated within the scope of my invention.

When using as a source of cinnamaldehyde having one or both of the structures:

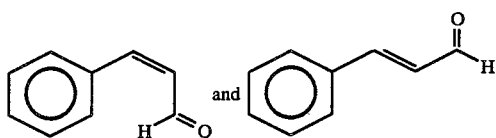

cinnamon oil or oil of cassia oil, the cinnamon oil or oil of cassia is admixed with water or a $C_1$–$C_5$ alcohol or a mixture of water and a $C_1$–$C_5$ lower alkanol as well as the base, e.g., sodium carbonate, sodium bicarbonate, potassium carbonate, potassium bicarbonate, lithium carbonate, lithium bicarbonate, calcium hydroxide, calcium carbonate, magnesium hydroxide, magnesium carbonate, proline having the structure:

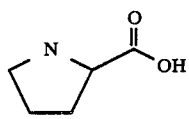

choline having the structure:

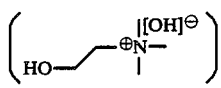

or lecithin-base mixture with the lecithin having the structure:

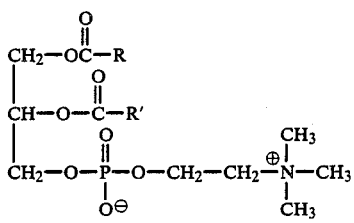

wherein the moieties:

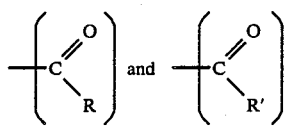

are defined, supra, the reaction mixture is then refluxed or heated for a period of between about 5 hours and about 80 hours. During the reaction it is desirable to remove the benzaldehyde-rich reaction product as it is formed. Hence, the benzaldehyde-rich reaction product may be removed overhead through a packed vertical reflux column connected to a cooling heat exchanger as illustrated in FIGS. 7A, 7B or 7C, infra. The product thus obtained exists in two phases; an upper aqueous phase and a lower more dense benzaldehyde-rich phase which can be separated from each other using a phase splitter; or the benzaldehyde-rich phase is separated from the aqueous phase, for example, by solvent extraction using such solvents as diethyl ether, dimethyl ether, hydrocarbons or methylene dicholoride, and the benzaldehyde-rich phase may then be fractionally distilled. The acetaldehyde may be separated from the benzaldehyde by means of the use of a high efficiency fractionation column and cooling heat exchanger. As will be seen in FIG. 7A, the acetaldehyde may be separated by trapping said acetaldehyde in a "cold trap".

Lecithin according to the "The Merck Index", Tenth Edition, Published by Merck & Company, Inc. of Rahway, N.J., 1983, at Monograph 5271 indicates that lecithins use is:

"edible and digestible surfactant and emulisifer of natural origin . . . "

The reference "The Merck Index", Tenth Edition, 1983 is incorporated by reference herein. The lecithin is an "ionic" surfactant or emulsifier as is seen from its structure set forth, supra and as is seen from the teachings of the Merck Index reference cited, supra.

Thus, at the end of the reaction or at the end of the desired time period for proceeding with the reaction, the "natural" benzaldehyde and "natural" acetaldehyde are fractionally distilled yielding a mixture rich in natural benzaldehyde and/or acetaldehyde. The benzaldehyde-rich fraction also may contain a considerable proportion of unreacted cinnamaldehyde. This resulting product may, if desired, be again fractionally distilled in order to enrich the benzaldehyde stream. From a practical standpoint such a mixture of cinnamaldehyde and benzaldehyde produced according to the first fractional distillation is usually adequate for use in food flavors, for example, or in tobacco flavors, for example.

Normally, but not necessarily, the acetaldehyde is prepared free of aromatic aldehydes for use in food flavors.

From a practical standpoint, the mixtures of acetaldehyde, benzaldehyde and cinnamaldehyde thus produced have unobvious, unexpected and advantageous properties for augmenting or enhancing the aroma or taste of consumable materials including but not limited to foodstuffs, chewing gums, medicinal products, toothpastes, chewing tobaccos, smoking tobacco and smoking tobacco articles, particularly almond, orange and cherry flavored foodstuffs and medicinal products.

The range of mole ratio of natural base to cinnamaldehyde (contained in the cinnamaldehyde-bearing natural substance, e.g., cassia oil, cinnamon bark, cinnamon leaf and the like) may vary from about 0.1:1 up to about 4:1. This mole ratio is based upon the following:

(a) Whether the reaction is carried out on a solid containing the cinnamaldehyde such as pulverized cinnamon bark in admixture with the base such as magnesium hydroxide (in which case the higher end of the range of mole ratios is applicable); or whether the reaction is a liquid phase reaction carried out in the presence of a base such as choline, proline or aqueous sodium bicarbonate with cinnamon oil and water, alcohol or an aqueous alcohol mixture (in which case the mole ratio of base:cinnamaldehyde is at the lower end of the above-mentioned range;

(b) The nature of the total energy input to the reaction; based upon heat input and time of reaction as well as temperature and pressure of reaction (thus, a relatively long time of reaction e.g., 80 hours will give rise to a higher "yield" of benzaldehyde and acetaldehyde and a lower concentration of cinnamaldehyde in the reaction product). Depending upon the flavorist's requirements, it may be desirable to create an ultimate composition containing, for example, greater than 80% benzaldehyde or a 50:50 mixture of benzaldehyde and cinnamaldehyde or substantially pure acetaldehyde (having present therewith minor quantities of other low boiling components such as crotonaldehyde and acetic acid); and (c) The particle size (where applicable) of the solid source of cinnamaldehyde, e.g., pulverized cinnamon bark or pulverized high cinnamaldehyde-containing cinnamon leaf. A small particle size will give rise to a faster conversion of cinnamaldehyde (contained in the solid cinnamaldehyde-bearing source) to benzaldehyde and acetaldehyde.

In all cases, our invention is capable of yielding in a controllable fashion desired ratios of benzaldehyde and acetaldehyde to cinnamaldehyde depending upon the reaction conditions employed.

The reaction product containing the cinnamaldehyde, benzaldehyde and acetaldehyde produced according to reaction:

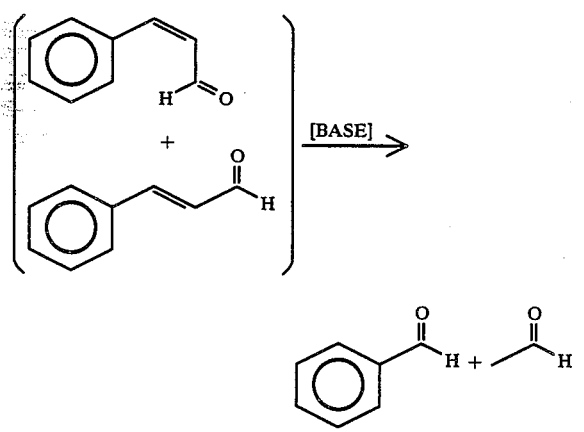

may be considered as a "natural" product. This "natural" product may be used "as is" or it may preferably be physically purified by such methods as fractional distillation and/or preparative chromatography. The resulting "natural" products will have novel utilities in augmenting or enhancing the aroma or taste of consumable materials including but not limited to foodstuffs, chewing gums, medicinal products, toothpastes, chewing tobaccos and smoking tobaccos particularly cherry flavored, orange flavored, almond flavored foodstuffs and medicinal products. Accordingly, for example, compositions of matter containing mole ratios of from about 10:90 up to about 99.9:0.1 of benzaldehyde:cinnamaldehyde in their natural state prepared according to the reaction:

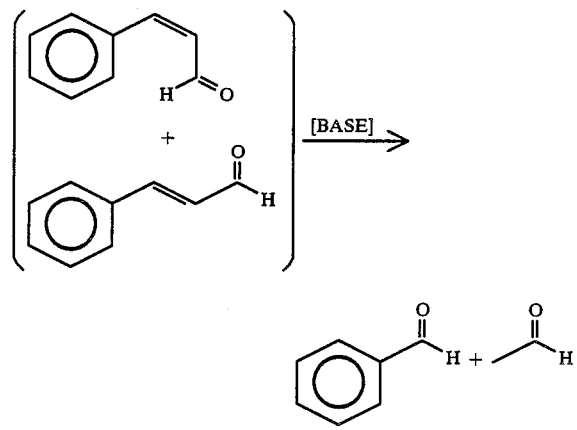

may be utilized in such consumable materials, e.g., foodstuffs as, for example, macaroon cookies, maraschino cherries, cherry flavored beverages such as carbonated cherry drinks, and the like.

Furthermore, substantially pure acetaldehyde containing minor amounts of impurities may be utilized in such consumable materials, e.g., foodstuffs such as orange drinks.

Collectively, these aforementioned benzaldehyde, cinnamaldehyde and acetaldehyde-containing products of my invention are hereinafter called "aldehyde-containing compositions".

The novel products of my invention may be utilized in foodstuffs and beverages in an amount of from about 0.5 ppm up to about 3% by weight of the resulting foodstuff or beverage. The materials can be used in such high percentages because of the manner in which they are produced; that is, free of any nitrile-containing substances as would be present if the aldehyde-containing products were produced from such materials as apricot kernels.

As used herein, the term "foodstuff" includes both solid and liquid ingestible materials which usually do, but need not, have nutritional value. Thus, foodstuffs includes soups, convenience foods, beverages, dairy products, candies, vegetable cereals, soft drinks, snacks and the like.

As used herein, the term "medicinal products" includes both solids and liquids which are ingestible non-toxic materials which have medicinal value such as cough syrups, cough drops and chewing medicinal tablets.

The term "chewing gum" is intended herein to be a foodstuff composition comprising a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine and a flavoring composition which incorporates one or more of the aldehyde-containing compositions of my invention and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable" and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthetically pleasing aroma and taste profile. Such material, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl) cellulose and methyl cellulose; natural and synthetic gums such as gum arabic, gum tragacanth, gelatin, proteinaceous materials; lipids; carbohydrates; starches, pectins and emulsifiers, e.g., mono- and diglycerides of fatty acids, skim milk powder, hexose, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate ammonium bicarbonate, ammonium phosphate, citric acid, lactic acid, vinegar and the like, colorants, e.g., carminic acid, cochineal, tumeric and curcumin and the like, firming agents such as aluminum sodium sulfate, calcium chloride and calcium glyconate, texturizers, anti-caking agents, e.g., aluminum calcium sulfate and tribasic calcium phosphate, enzymes, yeast foods, e.g., calcium lactate and calcium sulfate, nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-cis-3-pentenoic acid; ketones and aldehydes other than the aldehyes of the aldehyde-containing compositions of our invention, e.g., acetophenone, acetone, acetyl methyl carbinol, acrolein, n-butanal, crotonal, diacetyl, beta,-beta-dimethyl-acrolein, n-hexanal, 2-hexanal, cis-3-hexenal, 2-heptenal, 4-(p-hydroxyphenyl)-2-butanone, alpha-ionone, beta-ionone, 2-methyl-3-butanone, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate, esters, such as butyl acetate ethyl acetate, ethyl acetoacetate; ethyl benzoate, ethyl butyrate, ethyl cinnamate, ethyl crotonate, ethyl formate, ethyl isobutyrate, ethyl isovalerate, ethyl alpha-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methyl-butyrate, propyl acetate, amyl acetate, amyl butyrate, benzyl salicylate, dimethyl anthranilate, ethyl methylphenylglycidate ethyl succinate isobutyl cinnamate and terpenyl acetate; essential oils such as jasmin absolute, rose absolute, orris absolute, lemon essential oil, Bulgarian rose, yara yara, natural raspberry oil and vanilla; lactones, sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the cyclic chemical compounds can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as varioua cellulose derivatives.

As will be appreciated by those skilled in the art, the amount of aldehyde-containing composition of my invention employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected (to be effective) be sufficient to augment or enhance the organoleptic characteristics of the parent composition (whether foodstuff per se or flavoring composition).

The use of insufficient quantities of aldehyde-containing composition of my invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food composition, it is found that quantities of aldehyde-containing composition of my invention ranging from a small but effective amount, e.g., 0.5 ppm up to 3% by weight based on total composition are suitable as stated, supra. Concentrations in excess of the maximum quantity stated are not normally recommended, since they fail to provide commensurate enhancement of organoleptic properties. In those instances where the aldehyde-containing composition of my invention is added to the foodstuff as an integral component of a flavoring composition, it is, of course, essential that the total quantity of flavoring composition employed be sufficient to yield an effective amount of aldehyde-containing composition.

Food flavoring compositions prepared in accordance with the present invention preferably contain the aldehyde-containing composition of my invention ranging from about 0.1% up to about 100% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the aldehyde-containing composition of my invention with, for example, gum arabic, gum tragacanth, carrageenan and the like, and thereafter spray-drying the resultant mixture whereby to obtain the particulate solid product. Pre-prepared flavor mixes in powder form, e.g., a fruit flavored powdered mix, are obtained by mixing the dried solid components, e.g., starch, sugar and the like and aldehyde-containing composition in a dry blender until the requisite degree of uniformity is achieved.

The novel aldehyde composition-containing substances produced according to the novel process of my invention may be used "as is" as stated, supra or may be used in conjunction with other flavor adjuvants including but not limited to:
Heliotropin;
Terpinenol-4;
Anisaldehyde;
Phenyl acetaldehyde;
Benzyl formate;
Benzyl acetate;
Cis-3-hexenyl benzoate;
Methyl Hexanoate;
Hexanal;
Eucalyptol;
Eugenol;
Ethyl acetate;
Ethyl butyrate;
Turpentine gum oil;
Limonene;
Gum camphor;
Isobornyl acetate;
Borneol;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpenyl acetate;
Gamma-undecalactone;
Vanilla;
Alochol;
Oil of Cubeb;
Phellandrene;
Beta-phellandrene;
Oil of Coriander;
Oil of Pimento Leaf;
Oil of Patchouli;
Alpha-Pinene;
Beta-Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg;

Cardamon oil;
Clove Oil;
Spearmint Oil; and
Oil of Peppermint.

An additional aspect of my invention provides an organoleptically improved smoking tobacco product and additives therefor, as well as methods of making the same which overcome specific problems heretofore encountered in which specific desired sweet and fruity flavor characteristics of natural tobacco are created or enhanced and may be readily controlled and maintained at the desired uniform level regardless of variations in the tobacco components of the blend.

This invention further provides improved tobacco additives and methods whereby various desirable sweet and fruity flavoring characteristics may be imparted to smoking tobacco products and may be readily varied and controlled to produce the desired uniform flavoring characteristics.

In carrying out this aspect of my invention, I added to smoking tobacco materials or a suitable substitute therefor (e.g., dried lettuce leaves) or I added to filters for smoking tobacco articles (e.g., cellulose acetate filters) an aroma and flavor additive containing as an active ingredient the aldehyde-containing composition of my invention which is the benzaldehyde/cinnamaldehyde composition.

In addition to the benzaldehyde/cinnamaldehyde composition of my invention other flavoring and aroma additives may be added to the smoking tobacco material or substituted therefor either separately or in admixture with the benzaldehyde/cinnamaldehyde composition of my invention as follows:

I. SYNTHETIC MATERIALS

Beta-ethyl-cinnamaldehyde;
Eugenol;
Dipentene;
Beta-Damascenone;
Maltol;
Ethyl maltol;
Delta undecalactone;
Delta decalactone;
Amyl acetate;
Ethyl butyrate;
Ethyl valerate;
Ethyl acetate;
2-Hexenol;
1,2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naptho-[2,1-b]-furan;
4-Hydroxy hexanoic acid, gamma lactone;
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg oil;
Origanum oil;

An aroma and flavoring concentrate containing the benzaldehyde/cinnamaldehyde composition of my invention and, if desired, one or more of the above indicated additional flavoring materials may be added to the smoking tobacco material, to the filter or to the leaf or paper wrapper. The smoking tobacco material may be shredded, cured, cased and blended tobacco material or reconstituted tobacco material or tobacco substitutents (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the benzaldehyde/cinnamaldehyde composition of my invention to smoking tobacco material is between 5 and 100 ppm (0.0005–0.01%) of the active ingredients to the smoking tobacco material. We have further found that satisfactory results are obtained if the proportion by weight of the sum total of benzaldehyde/cinnamaldehyde composition of my invention used to flavoring material is between 50 and 1000 ppm (0.005–0.1%).

Any convenient method for incorporating the benzaldehyde/cinnamaldehyde composition of my invention in the tobacco product may be employed. Thus, the benzaldehyde/cinnamaldehyde composition of my invention taken alone or along with other flavoring additives may be dissolved in a suitable solvent such as ethanol, pentane, diethyl ether and or other volatile organic solvents and the resulting solution may either be spread on the cured, cased and blended tobacco material or the tobacco material may be dipped into such solution. Under certain circumstances, a solution of the benzaldehyde/cinnamaldehyde composition of our invention taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substituted therefor need be treated and the thus treated tobacco may be blended with other tobaccos before the ultimate tobacco product is formed.

In such cases, the tobacco treated may have the benzaldehyde/cinnamaldehyde composition of my invention in excess of the amounts or concentrations above indicated so that when blended with other tobaccos, the final product will have the percentage within the indicated range. In accordance with one specific example of my invention, an aged, cured and shredded domestic burley tobacco is spread with a 20% ethyl alcohol solution of a mixture containing 75% benzaldehyde and 25% cinnamaldehyde prepared by carrying out a reaction in a "Soxhlet" apparatus of the type set forth in FIG. 4 using an $Mg(OH)_2$ catalyst. The amount of benzaldehyde/cinnamaldehyde composition is 20 ppms on a dry basis. Thereafter, the alcohol is removed by evaporation and the tobacco is manufactured into cigarettes by the usual techniques. The cigarette when treated as indicated has a desired and pleasing sweet and fruity aroma with faint aesthetically pleasing cherry nuances which is detectable in the main and side streams when the cigarette is smoked. The aroma is described as being sweeter, rich, less harsh, more tobacco-like and having fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, the benzaldehyde/cinnamaldehyde compositions of our invention can be incorporated with materials such as filter tip materials, seam paste, packaging materials and the like which are used along with tobacco to form a product adapted for smoking. Furthermore, the benzaldehyde/cinnamaldehyde compositions of my invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

BRIEF DESCRIPTION OF THE DRAWINGS

FIG. 4 is a cut-away cross sectional elevation view of a Soxhlet apparatus used for carrying out the reaction:

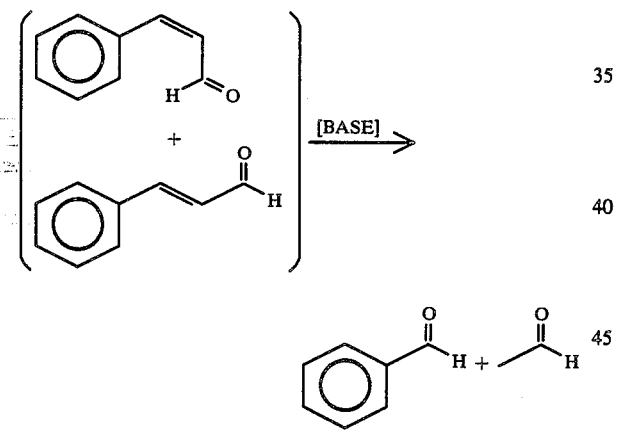

when the cinnamaldehyde is present in a solid material such as pulverized cinnamon bark and when the basic catalyst is a solid such as magnesium hydroxide or calcium hydroxide.

FIG. 5 is a simplified Soxhlet reaction apparatus fitting for carrying out the reaction:

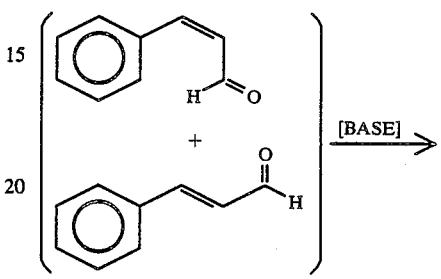

-continued

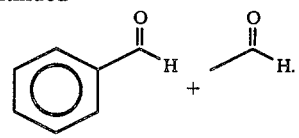

FIG. 6 is a diagram of a solid-liquid phase reaction apparatus useful in carrying out the retro-aldol reaction, to wit:

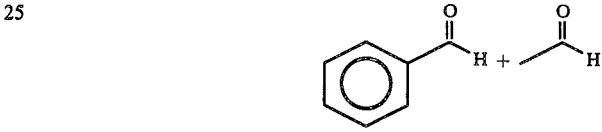

when the cinnamaldehyde having the structure:

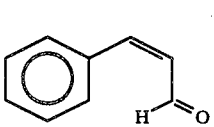

or

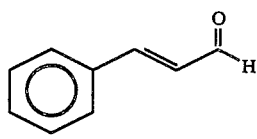

or a mixture thereof is in existence in a natural solid material such as cinnamon bark.

FIG. 7 is a diagram of a liquid-liquid phase apparatus for carrying out the reaction:

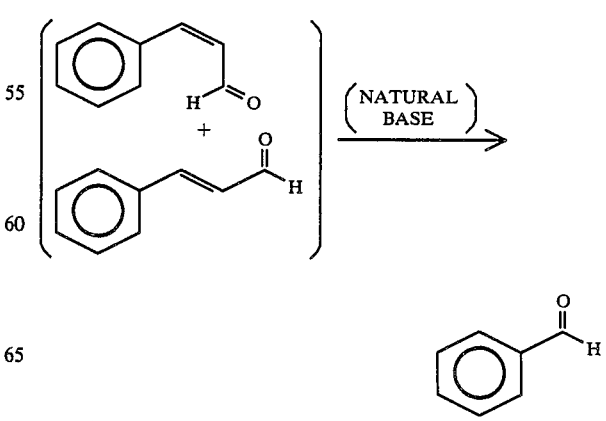

and recovering the natural benzaldehyde-containing composition of my invention (as employed in Example VI, infra).

Figures 7A, 7B:
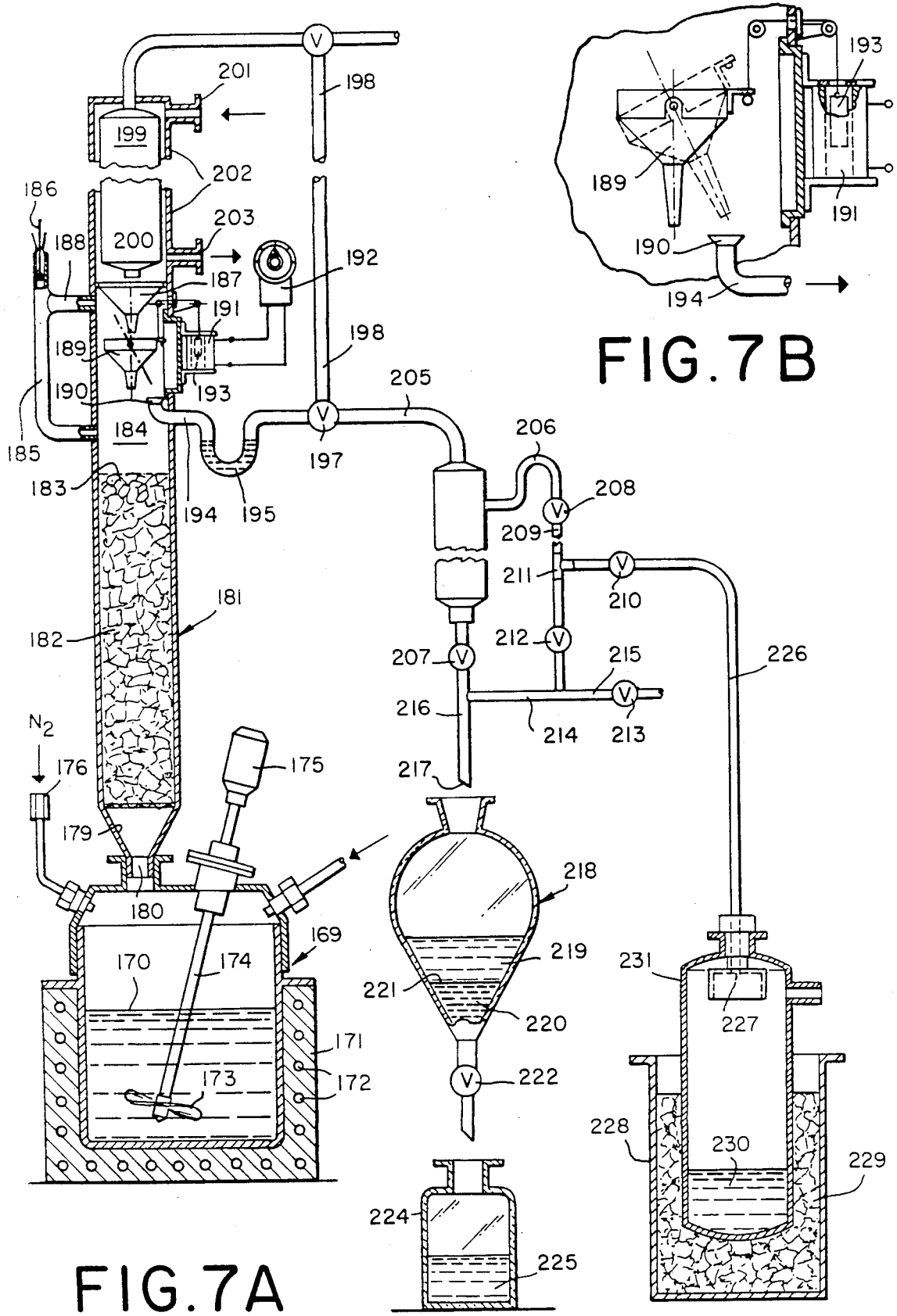

FIG. 7A is a diagram of a liquid-liquid phase reaction and recovery apparatus for carrying out the reaction:

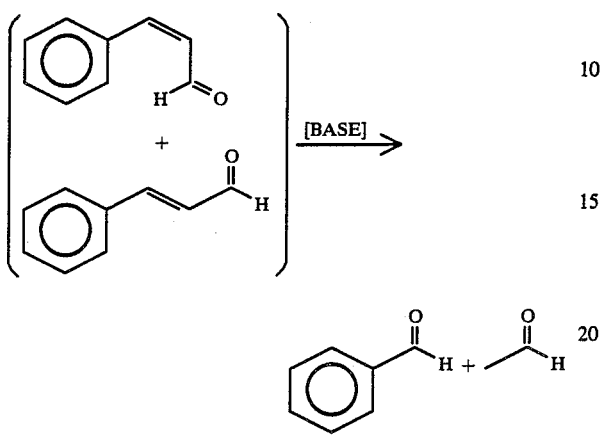

and recovering the natural-benzaldehyde-containing composition and the natural acetaldehyde-containing composition of my invention (as employed in Example VI, infra).

FIG. 7B is a diagram of a section of the apparatus of FIG. 7A showing the magnetic coil-actuated recovery-return mechanism of the apparatus useful in the practice of our invention.

Figure 7C:
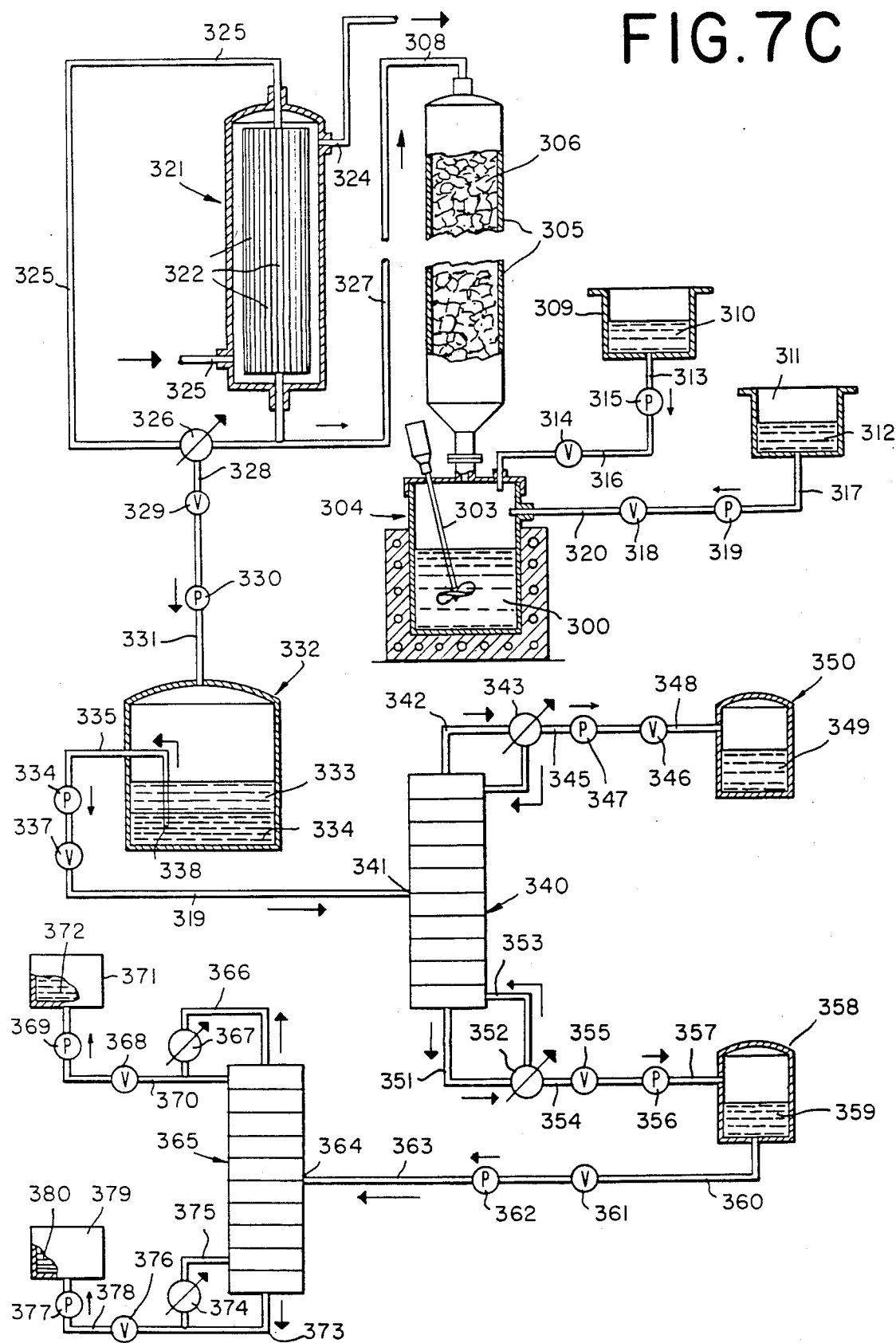

FIG. 7C is a diagram of a continuous liquid-liquid phase reaction-recovery apparatus for carrying out the reaction:

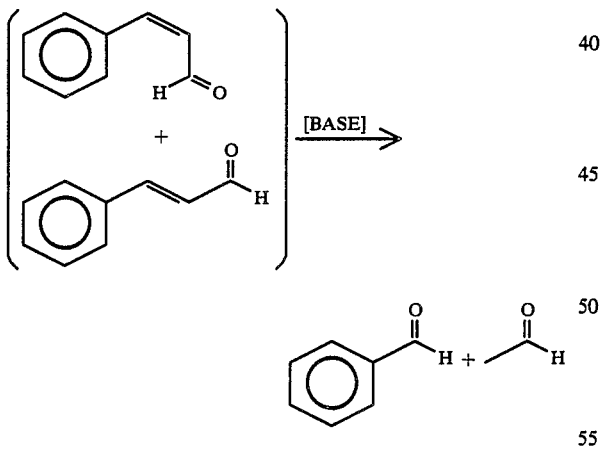

and recovering the natural benzaldehyde-containing composition and natural acetaldehyde-containing composition of our invention.

Figure 8:
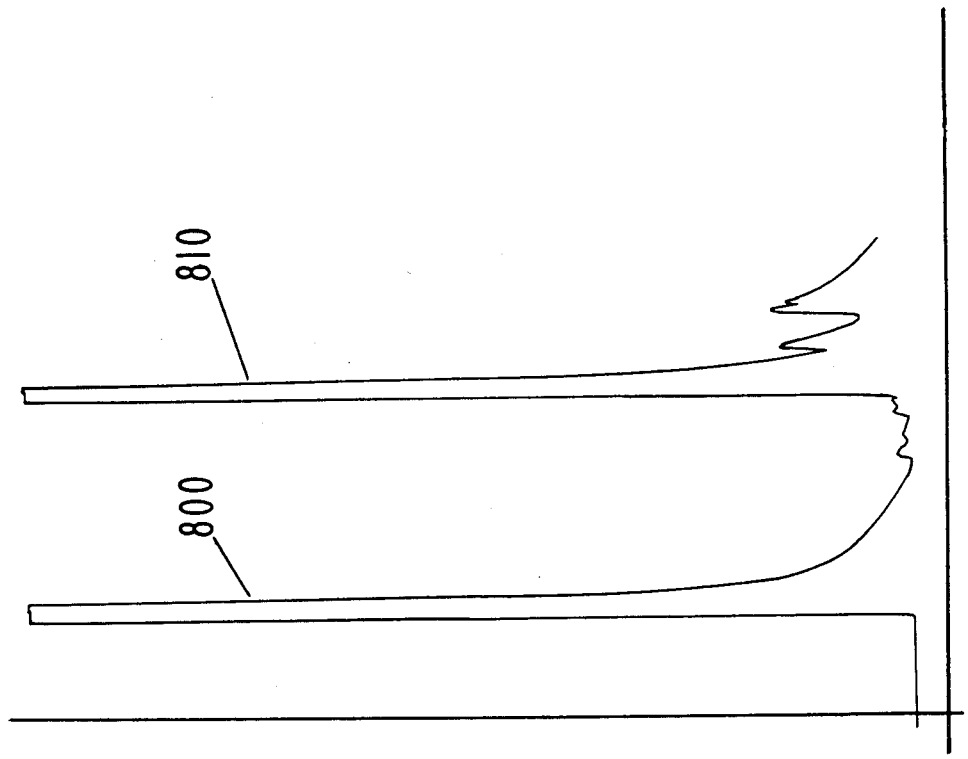

FIG. 8 is the GLC profile of the reaction product produced according to Example VI containing benzaldehyde and cinnamaldehyde.

Figure 9:
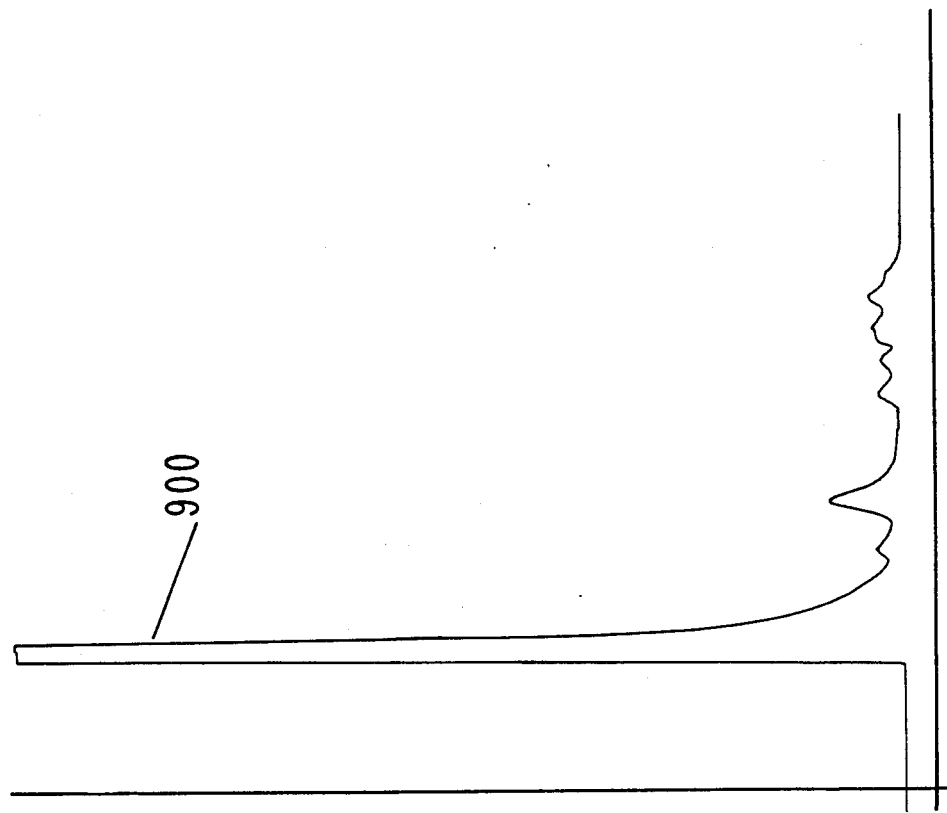

FIG. 9 is the GLC profile of a first distillation product of the reaction product of Example VI rich in benzaldehyde.

Figure 10:
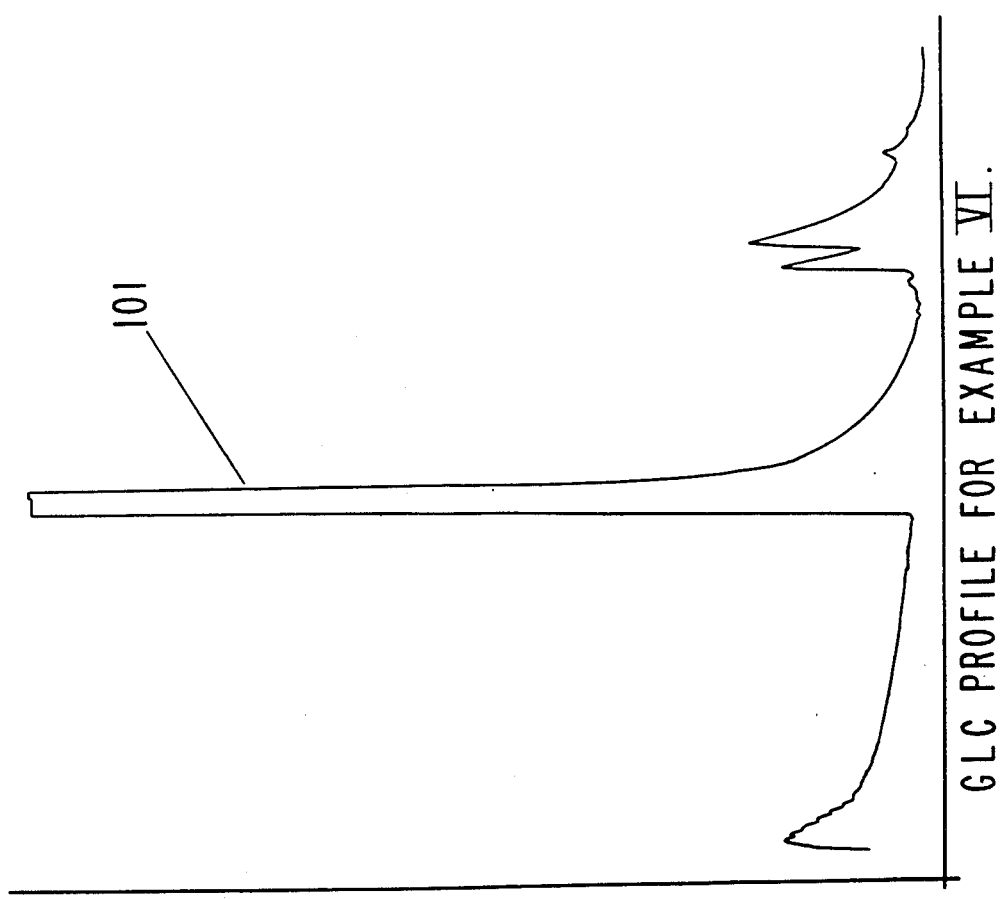

FIG. 10 is the GLC profile of a second distillation product of the reaction product of Example VI rich in benzaldehyde.

Figure 11:
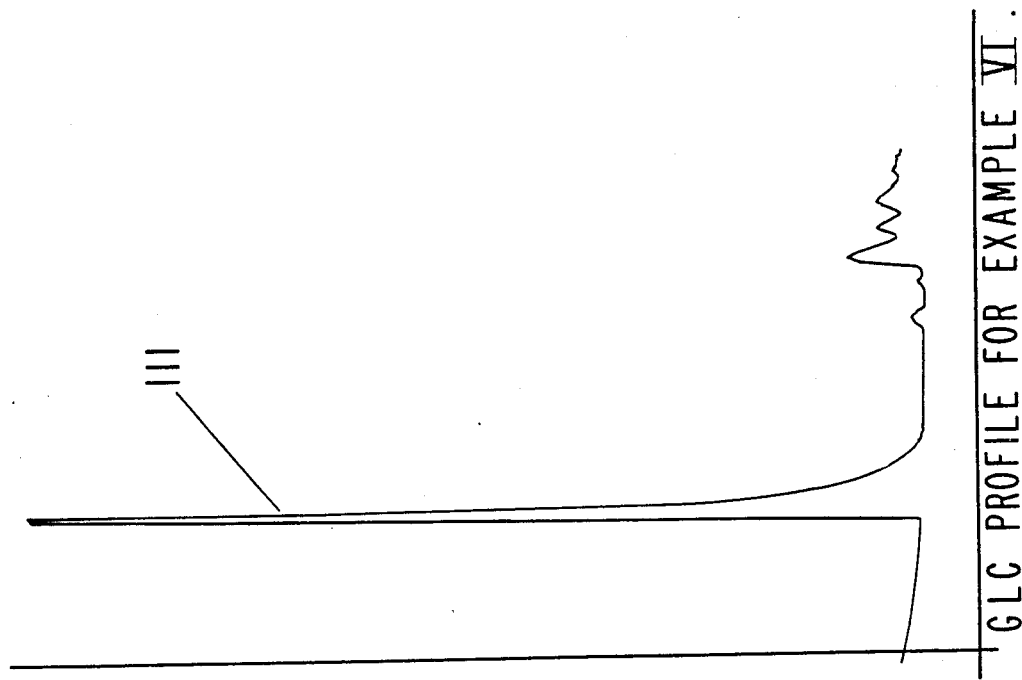

FIG. 11 is the GLC profile of a third distillation product of the reaction product of Example VI rich in benzaldehyde.

FIG. 12 is a total ion current spectrum of a GC-MS analysis of acetaldehyde-rich product recovered in cold trap 231 of the apparatus of FIG. 7A.

DETAILED DESCRIPTION OF THE DRAWINGS

Figure 1:
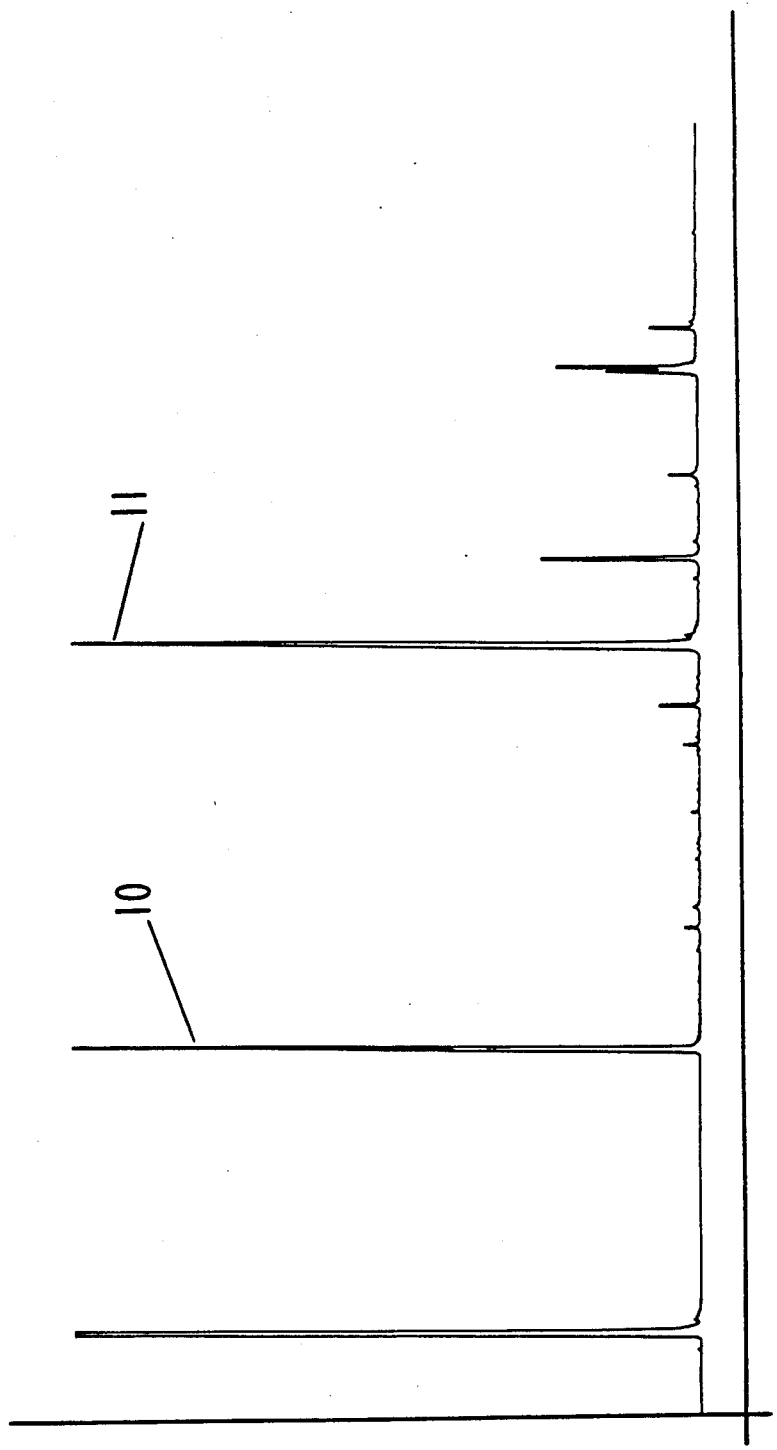
FIG. 1 is the GC-IR spectrum for the reaction product of Example I containing benzaldehyde and cinnamaldehyde.

FIG. 1 is the GC-IR spectrum for the crude reaction product of Example I. The peak indicated by reference numeral 10 is the peak for benzaldehyde in the reaction product. The peak indicated by reference numeral 11 is the peak for cinnamaldehyde having the structures:

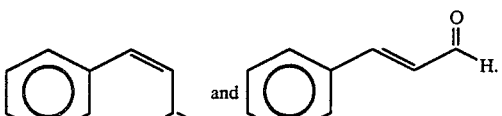

Figure 2:
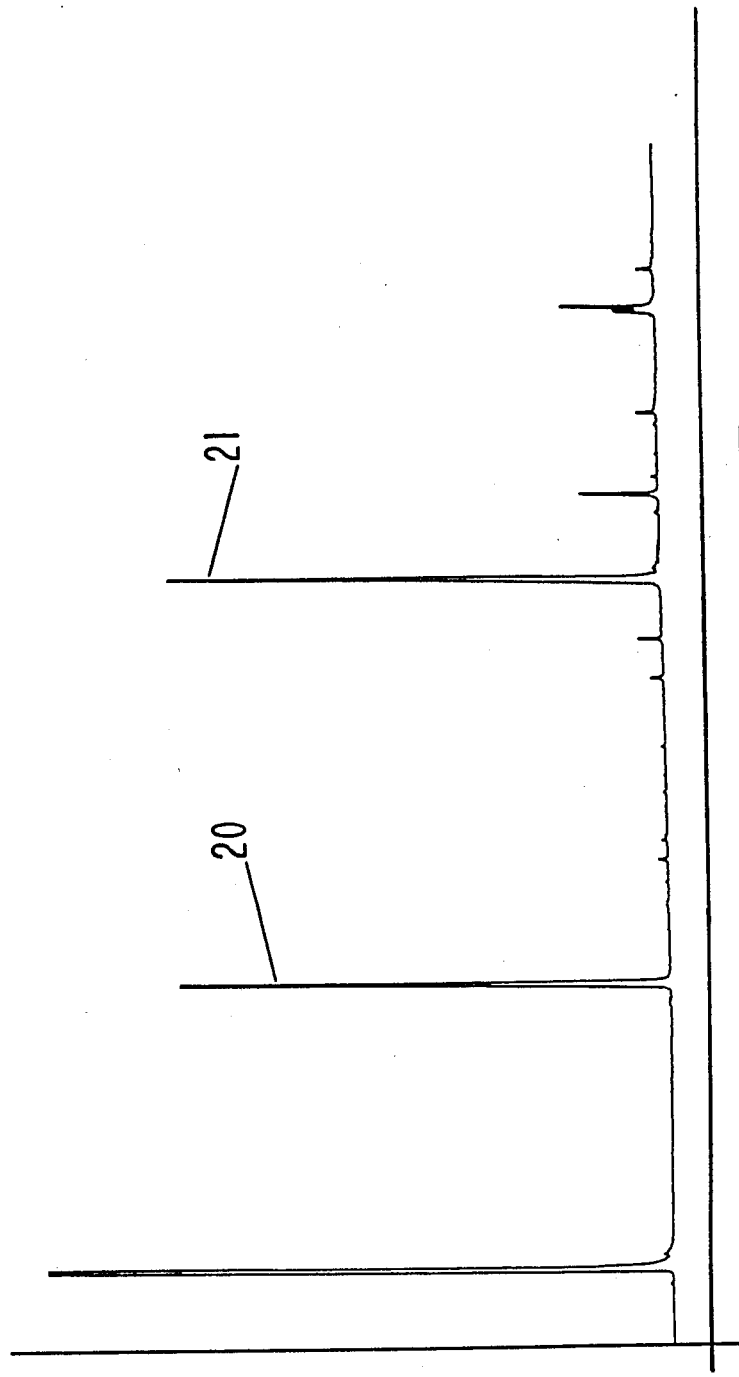
FIG. 2 is a GC-IR spectrum for the distillation residue of Example I containing cinnamaldehyde and benzaldehyde.

FIG. 2 is the GC-IR spectrum for the distillation residue of Example I containing benzaldehyde and cinnamaldehyde. The peak indicated by reference numeral 20 is the peak for benzaldehyde. The peak indicated by reference numeral 21 is the peak for the unreacted cinnamaldehyde having the structure:

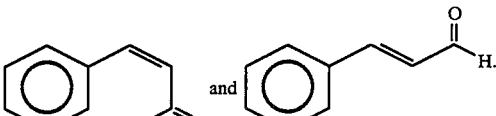

Figure 3:
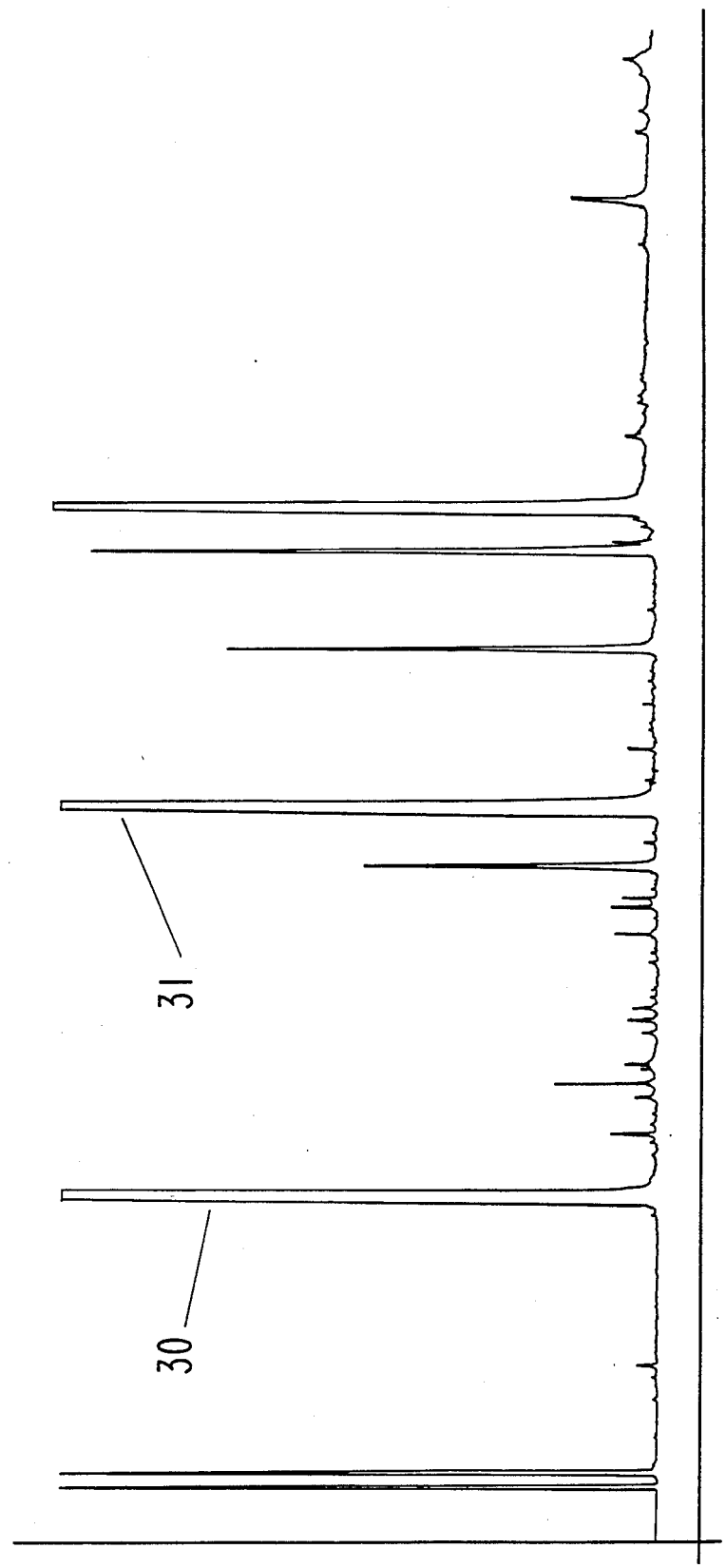
FIG. 3 is a GC-IR spectrum for the reaction product of Example II containing benzaldehyde and cinnamaldehyde (Conditions: Carbowax column programmed at 75°–225° C. at 3° C. per minute).

FIG. 3 is the GC-IR spectrum for the crude reaction product of Example II. The peak indicated by reference numeral 30 is the peak for benzaldehyde. The peak indicated by reference numeral 31 is the peak for cinnamaldehyde.

The apparatus of FIG. 4 (the Soxhlet reaction apparatus) is used to effect the reaction:

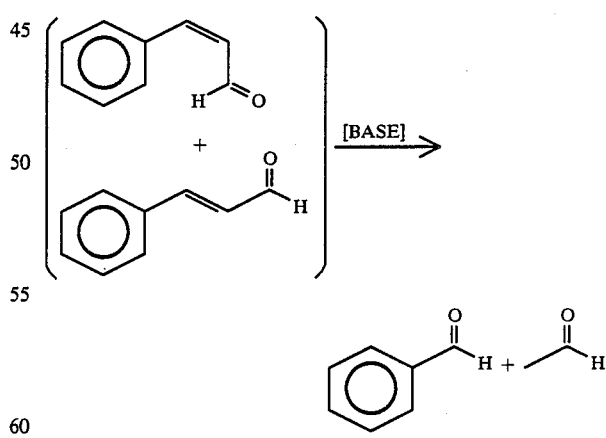

when the cinnamaldehyde is present in such solid materials as pulverized cinnamon bark.

The mixture of cinnamaldehyde-bearing material (e.g., pulverized cinnamon bark ceylon) and solid natural base, (for example, limestone or lecithin) 46 is placed in a porous thimble 45 (the thus-filled porous thimble is placed in the inner tube 42 of the Soxhlet apparatus).

The apparatus is then fitted to a bolt-head flask 41 containing water or a mixture of water and a $C_1-C_4$ lower alkanol, e.g., methanol, ethanol, isopropanol, n-propanol, n-butanol, isobutanol, t-butanol, t-amyl alcohol or n-amyl alcohol and to reflux condenser 57 having a cooling jacket 54 fitted with cooling liquid inlet tube 55 surrounding a condenser surface 53. The reflux condenser having outlet 56 is tightly fitted via stopper 52 to the inner tube 42 of the Soxhlet apparatus. The solvent, the water the alkanol or the water-alkanol mixture is boiled at location 40 in flask 41. The vapor passes up through the tube 44 and is condensed by condenser 57 and the condensed solvent falls from 53 through opening 56 into the thimble 45 and slowly fills the body of the apparatus 47. When the water or $C_1-C_4$ alkanol or the water $C_1-C_5$ lower alkanol mixture contacts the mixture of pulverized cinnamaldehyde-bearing and solid base (.g., $Mg(OH)_2$ in thimble 45, a retro-aldol reaction is effected, thusly:

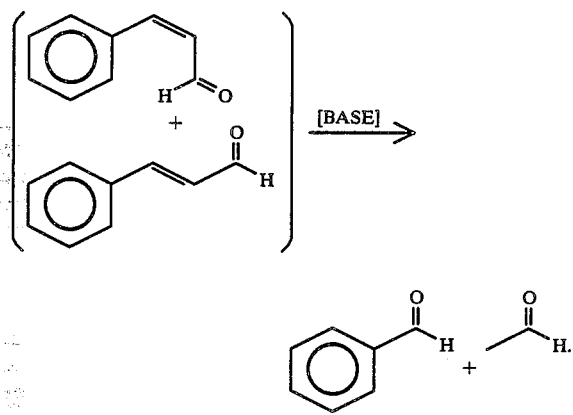

The result of this reaction is the formation of a water-cinnamaldehyde-benzaldehyde-acetaldehyde mixture or a water-cinnamaldehyde-benzaldehyde-acetaldehyde $C_1-C_5$ lower alkanol mixture. The solid-liquid reaction mass residence time in the thimble must be sufficient to allow a final yield of benzaldehyde and acetaldehyde in amounts of 10% or more.

When the mixture reaches the top of tube 43, it siphons over through tube 43 into flask 41 and thus effects removal of that portion of the reaction product which is "extracted" in thimble 45. The process is repeated automatically as the reaction proceeds in thimble 45, that is, the retro-aldol reaction, to wit:

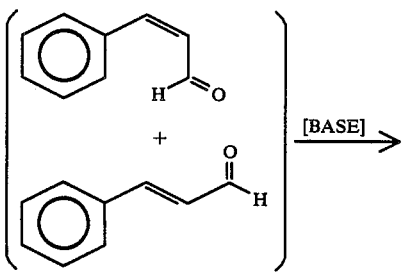

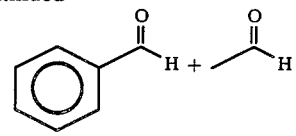

proceeds in thimble 45. The resulting "natural" benzaldehyde may be isolated as by fractional distillation.

In place of the solid base, e.g., $Mg(OH)_2$ at location 46, a lecithin-base mixture (lecithin is a chloline precursor having the structure:

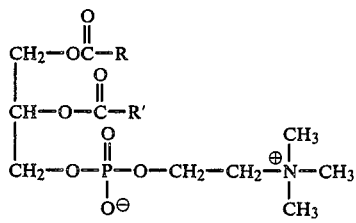

wherein the moieties:

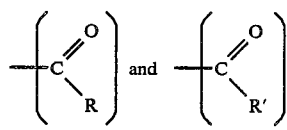

have been defined, supra) may be added at location 40 (with the reaction taking place at location 40 rather than at location 46 or a natural proline or choline embedded in an inert polymer having micropores such as microporous polyethylene may be admixed with the cinnamaldehyde-bearing solid, e.g., the pulverized cinnamon bark at location 46.

In the case of the reaction taking place at location 46, the siphon tube 43 has an outlet into the flask 41 at 51 wherein the reaction product containing large amounts of benzaldehyde together with water or water/alkanol mixture is passed through the opening 51 of siphon tube 43 and then through the opening of the Soxhlet apparatus into flask 41. The Soxhlet apparatus is firmly in place in a vapor-tight manner as a result of the placement of tube 49 in tightly-fitting stopper 48 located in the neck of flask 41 at location 50.

In the case of the reaction taking place at location 41, the siphon tube 43 has an outlet into the flask 41 at 51 wherein extracted cinnamaldehyde together with water, alkanol or water/alkanol mixture is passed through the opening 51 of siphon tube 43 and then through the opening of the Soxhlet apparatus into flask 41. The Soxhlet apparatus is firmly in place in a vapor-tight manner as a result of the placement of tube 49 in tightly-fitting stopper 48 located in the neck of flask 41 at location 50.

In place of Soxhlet apparatus and tube 42, the retro-aldol reaction can take place in an apparatus of the nature of FIG. 5.

Referring now to FIG. 5, the solid cinnamaldehyde-containing material, for example, pulverized cinnamon bark may be placed on a sintered glass disc 70 of FIG. 5 and the entire apparatus may be fitted onto a reaction vessel which is also fitted with a distillation apparatus. Hot $C_1-C_5$ or hot alkanol-water mixture or hot water may be added through opening 73 into tube 71 slowly passed the pulverized cinnamaldehyde containing material resting on sintered glass disc 70. The water, $C_1$–$C_5$ or the water/$C_1$–$C_5$ lower alkanol mixture may be admixed with a base such as proline choline, sodium bicarbonate, potassium bicarbonate, sodium bicarbonate, lithium carbonate or lithium bicarbonate or a mixture of lecithin and base. In the alternative, the cinnamaldehyde-yielding material may be admixed with solid base while resting on sintered glass disc 70. The entire apparatus is fitted at 72 into a flask having fitted thereto a distillation apparatus. As the benzaldehyde-rich reaction mixture passes through disc 70 through opening 74 into the flask it may be simultaneously distilled or it may be recycled if it contains an excessive amount of cinnamaldehyde that has not reacted and if it is desired to create a more enriched benzaldehyde-containing product.

FIG. 6 is a schematic diagram of a solid-liquid phase reaction apparatus which can be used to carry out the retro-aldol reaction of my invention, to wit:

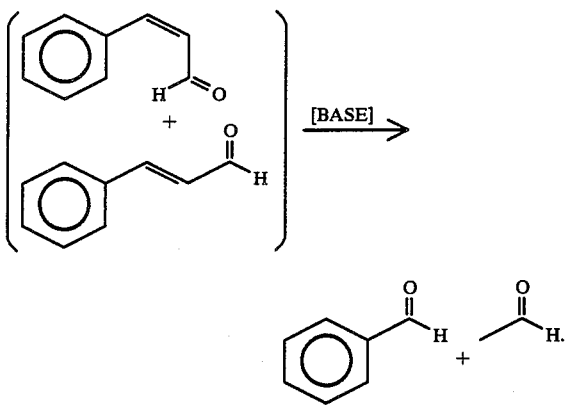

Set forth in FIG. 6 is a solid-liquid retro-aldol reaction apparatus which is specifically described in U.S. Pat. No. 1,636,550, the specification for which is incorporated herein by reference. Specifically, in FIG. 6, the numeral 2001 designates a holder for particularized cinnamaldehyde-bearing solid, for example, particularized cinnamon bark or cinnamon leaf which contains a large quantity of cinnamaldehyde having the structures:

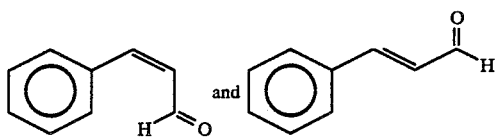

taken alone or mixed with a solid basic catalyst (e.g., Ca(OH)$_2$ or Mg(OH)$_2$) which is shown at 2002 in the drawing. Arranged below the holder is a vaporizing apparatus for reaction solvent, e.g., water, a $C_1$–$C_5$ lower alkanol or a mixture of $C_1$–$C_5$ lower alkanol and water (such as a 50:50 mixture of ethanol and water), which apparatus consists preferably of a closed container 2003 arranged in a heating bath vessel 2004 which may be a hot oil bath. Heat may be applied to vessel 2004 either by gas flame, steam coils located in the vessel, solar energy or any other suitable means. Connected with the holder 2001 is a condenser 2005. The condenser 2005 may be of any suitable construction. It is shown as consisting of a vessel provided with two interior headers 2006 and 2007 having a plurality of condensing tubes 2008. The space between the headers is supplied with a cooling fluid by means, for example, of a cold water inlet pipe 2009. 2010 is an outlet pipe for cooling fluid which fluid may, if desired, be artifically cooled before being introduced into the condenser to the extent necessary to completely condense the vaporized solvent to a temperature of 60°–80° C., for example, although this temperature will necessarily vary with the pressure in the holder.

Reference numeral 2011 indicates a pipe for conducting the vaporized water of lower alkanol or mixture of water and lower alkanol from vessel 2003 into the upper portion of the holder 2001. Reference numeral 2012 indicates a pipe leading from the lower portion of the holder to the vessel 2003, preferably. It is desirable to form pipe 2012 with an upward bend 2013 whereby the water or lower alkanol or mixture of water and lower alkanol will be accumulated in the holder to a certain level, that is to say, above the body of reaction mass, that is, the pulverized cinnamaldehyde-bearing solid materials such as pulverized cinnamon bark ceylon intimately admixed with solid basic catalyst, e.g., Mg(OH)$_2$ or Ca(OH)$_2$ before being discharged to vessel 2003. When the outflow from the holder is started, it is continued siphonically until the holder is emptied of liquid so that the action is intermittent. The solid-liquid reaction mass residence time in the thimble must be sufficient to allow a final yield of benzaldehyde and acealdehyde in amounts of 10% or more.

An evacuating mechanism is provided for maintaining a constant sub-atmospheric pressure in the holder, condenser and vapor-izing vessel 2003. For example, a vacuum pump 2014 may be connected by pipe 2015 to the top of the condenser 2005. The method of the retro-aldol reaction applied to the treatment of the cinnamaldehyde-bearing solid, e.g., pulverized cinnamon bark or pulverized cinnamon leaf, and using the apparatus as above described is as follows:

The pulverized cinnamaldehyde-bearing solid, e.g., cinnamon bark ceylon is comminuted and placed in the holder 2001. At a 1:1 mole ratio (for example) the solid basic catalyst, e.g., Mg(OH)$_2$ or MgO or CaO or Ca(OH)$_2$ is added to the pulverized cinnamaldehyde-bearing material (the mole ratio is based on the cinnamaldehyde determined to be in the pulverized cinnamaldehyde-bearing material) and allowed to stand under water, alcohol or an aqueous alcohol mixture such as a 50:50 mixture of ethyl alcohol and water for a period of time (e.g., 30–40 hours). The water, alkanol or aqueous alcohol mixture may be used in an amount approximating 40–60% by volume of the pulverized cinnamaldehyde-bearing material, e.g., cinnamon bark ceylon.

After the pulverized cinnamaldehyde-bearing solid, e.g., cinnamon bark has been macerated, in this manner, as long as necessary, a volume of water, alcohol or aqueous alcohol, e.g., 50:50 ethanol:water preferably equal to at least the volumetric contents of the holder 2001 is placed in vessel 2003 and the water or alcohol-water mixture in vessel 2004 is heated to a temperature in the range of 80°–100° C. (e.g., 85° C., for example, when a 50:50 mixture of ethanol and water is present) to bring about vaporization of the alcohol mixture. At the same time, the vacuum pump 2014 is started. The pump is operated so as to maintain a constant vacuum in the apparatus of from approximately 250 mm/Hg. pressure up to approximately 750 mm/Hg. pressure.

The vaporized solvent passes from vessel 2003 through pipe 2011 into the space 2016 above the material 2002 in holder and into the condenser 2005. Coming in contact with the water cooled tubes 2008, the vapor is condensed and is refluxed upon the pulverized cinnamaldehyde-bearing material (e.g., cinnamon bark) treated. As soon as the level of the liquid in the holder rises above the upper bend of siphon 2013, the solvent admixed with benzaldehyde-acetaldehyde and cinnamaldehyde is drawn from the bottom of the holder and discharged into vessel 2003 by the siphoning action described. The vaporization of the solvent and its condensation and precipitation on the pulverized cinnamaldehyde-bearing material, (e.g., cinnamon bark)—basic catalyst mixture (e.g., Mg(OH)$_2$) is continuous so that the extracting operation may be carried on as long as may be necessary in order to remove the reaction product, that is, the high benzaldehyde and acetaldehyde-containing reaction product from the pulverized cinnamaldehyde-bearing material, (e.g., cinnamon bark) to the extent desired. Ordinarily, the vaporization and condensation of the solvent will not keep pace with its discharge through the siphon so that the operation of the apparatus so far as withdrawal of the solvent and extraction is concerned, will be intermittent. That is, a certain amount of the solvent will collect and remain in contact for a time with the pulverized cinnamaldehyde-bearing material (e.g., pulverized cinnamon bark or pulverized cinnamon leaf) and then will be discharged, the holder being practically emptied of liquid before the siphoning action is stopped.

FIG. 7A is a schematic diagram of a liquid-liquid phase reaction-product recovery apparatus which can be used to carry out the retro-aldol reaction of my invention, to wit:

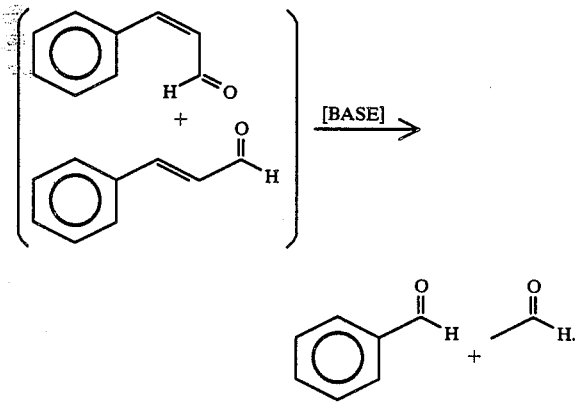

Set forth in FIG. 7A is a liquid-liquid retro-aldol reaction-product recovery apparatus which is composed of a reaction vessel 169 attached to a packed refluxing column 181 containing packing (e.g., Raschig Rings or Berle Saddles) 182 up to level 183, which, in turn, is connected to the condenser/vapor line/product recovery-return system (hereinafter referred to as the "CVPR" system. The "CVPR" system consists of vapor line 185 containing thermometer or temperature gauge 186 connected back into the main column through line 188; at the very top of the column is condenser 199 surrounded by cooling liquid in jacket 202 with the cooling liquid entering at 201 and exiting at 203. Fixed funnel 187 is located below condenser 199 which has opening 200 leading into fixed funnel 187. Liquid from fixed funnel 187 is directed into movable funnel 189 which is caused to be moved by means of magnet 193 operated using magnetic coil 191 using electric timer 192. Movable funnel 189 can cause liquid to be directed back onto packing surface 183 through space 184 or the liquid may be directed into tube 194 through opening 190. Hence, according to the way the electric timer is set, condensed liquid may intermittently be directed back into the packing or into recovery tube 194 past valve 197 through tube 205 past vavle 207 through tube 216 and opening 217 into separatory funnel 218. Material having a higher vapor pressure such as acetaldehyde proceeds through tube 206 past valve 208 passed "T" joint 211 through valve 210 and tube 226 through opening 227 into cold trap 231 wherein the substantially pure acetaldehyde containing minor impurities is collected (shown by reference numeral 230).

In carrying out the reaction:

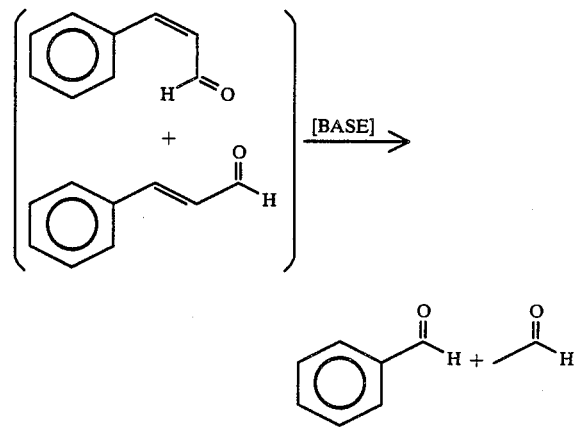

a liquid-bearing cinnamaldehyde substance, e.g., cassia oil or cinnamon oil or natural solvent-containing cassia oil or cinnamon oil 170 is placed in reaction vessel 169. Simultaneously, or subsequently base, e.g., sodium carbonate or sodium bicarbonate or proline or choline is placed in reaction vessel 169 with stirring by stirrer 173 powered by stirrer motor 175 through shaft 174. Simultaneously, a nitrogen blanket is maintained over the stirred reaction mass using nitrogen gas pumped in through opening 176 into the reaction vessel 169 at orifice 177. Reaction mass 170 may also contain water or a $C_1$–$C_5$ lower alkanol such as ethyl alcohol or a mixture of water and a $C_1$–$C_5$ lower alkanol. Heating mantle 171 containing heating elements 172 is energized while the stirrer motor is in operation causing the reaction mixture 170 to undergo a reaction whereby a mixture of cinnamaldehyde, acetaldehyde and benzaldehyde together with either of the $C_1$–$C_5$ alkanol solvent or the $C_1$–$C_5$ alkanols solvent/water mixture or water is vaporized through opening 180, and reaction flask neck 179 into packed column 181 containing packing 182 and having a packing surface at 183. The vapor is partially condensed in the packing 182 and the condensed material returns through the packing back into the reaction flask for subsequent reaction.

Simultaneously, part of the vapor proceeds through vapor tube 185 passed thermometer or temperature gauge 186 through tube 188 back into the column and onto condenser 199. With valve 197 open with respect to tube 198, highly volatile mixture containing acetaldehyde proceeds passed the condenser 199 through tube 198 passed tube 205 through tube 206 (with valves 208 and 210 "open") through tube 209 and through tube 226 into cold trap 231 through opening 227. Thus, substantially pure acetaldehyde is collected at 230 using dry ice trap 228 containing dry ice at location 229. Less volatile condensate (e.g., a mixture rich in cinnamaldehyde and benzaldehyde and containing smaller amounts of acetaldehyde is condensed at 199 and the condensate passes back through opening 200 into fixed funnel 187. The condensate then proceeds into movable funnel 189 wherein part of the condensate is returned through space 184 into packing 182 and then back into the reactor 169 for subsequent reaction and part of the condensate is directed into tube 194 through opening 190 intermittently as a result of the setting of electric timer 192 which operates magnetic coil 191 which actuates magnet 193 causing movable funnel 189 to move laterally; at one point in the time interval causing fluid to enter opening 190 and at another point in the time interval causing fluid to enter the packed column 181 through packing 182. Hence with valve 197 open with respect to tube 194–196, benzaldehyde/cinnamaldehyde reaction product passes through the "U" tube 195 past valve 197 through tube 205 past valve 207 (in open position) through tube 216 through opening 217 into separatory funnel 218 wherein water or mixture of water and alkanol or alkanol separates out. The benzaldehyde/cinnamaldehyde mixture is located at location 220 and the water or water/alkanol mixture of alkanol is at location 219 separated at phase separation location 221. When the separatory funnel fills, valve 222 is opened permitting benzaldehyde/cinnamaldehyde mixture 200 to proceed into product container 224 at location 225.

When valve 207 is open, simultaneously acetaldehyde vapors not condensing may still pass through tube 206 with valve 208 and valve 210 open and valve 212 and 213 closed with the acetaldehyde condensing in cold trap 231 cooled by dry ice 229 in container 228 otherwise vapors are vented to the atmosphere if valve 210 is closed and valves 208, 212 and 213 are open with the acetaldehyde passing through tube 206 and past tube 214. In addition, other vapors may pass through tube 215 through valve 213 into the open atmosphere.

Referring to FIG. 7B, FIG. 7B shows magnetic coil 191 in the vicinity of magnet 193 whereby movable funnel 189 may be moved so that the funnel may be positioned to direct liquid coming into same from funnel 187 either into tube 190 for recovery purposes or back onto packed column 181 (on packing 182) for recycle purposes.

Referring to FIG. 7C, FIG. 7C is a "continuous apparatus" version of the batch type apparatus of FIG. 7A.

In actuality, FIG. 7C is a schematic diagram of a continuous liquid-liquid phase reaction-product recovery apparatus which can be used to carry out the retro-aldol reaction of our invention, to wit:

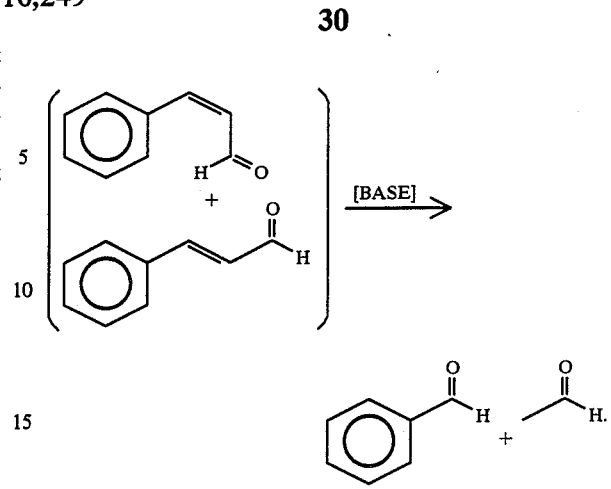

When valve 207 is open, simultaneously acetaldehyde vapors not condensing may still pass through tube 206 with valve 208 and valve 210 open and valve 212 and 213 closed with the acetaldehyde condensing in cold trap 231 cooled by dry ice 229 in container 228 otherwise vapors are vented to the atmosphere if valve 210 is closed and valves 208, 212 and 213 are open with the acetaldehyde passing through tube 206 and past tube 214. In addition, other vapors may pass through tube 215 through valve 213 into the open atmosphere.

Referring to FIG. 7B, FIG. 7B shows magnetic coil 191 in the vicinity of magnet 193 whereby movable funnel 189 may be moved so that the funnel may be positioned to direct liquid coming into same from funnel 187 either into tube 190 for recovery purposes or back onto packed column 181 (on packing 182) for recycle purposes.

Referring to FIG. 7C, FIG. 7C is a "continuous apparatus" version of the batch type apparatus of FIG. 7A.

In actuality, FIG. 7C is a schematic diagram of a continuous liquid-liquid phase reaction-product recovery apparatus which can be used to carry out the retro-aldol reaction of our invention, to wit:

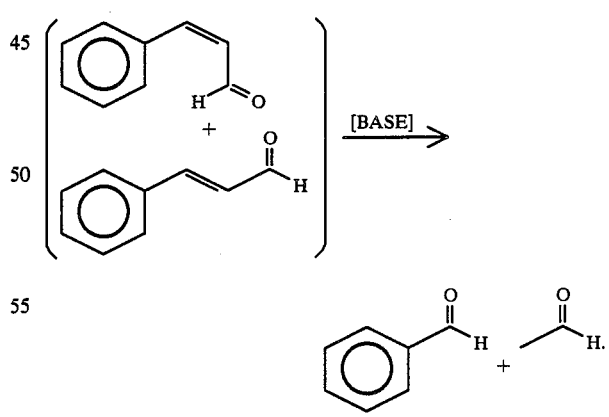

Set forth in FIG. 7C is a liquid-liquid retro-aldol reaction-product recovery apparatus which is composed of a reaction vessel 304 attached to a packed refluxing column 305 containing packing 306 which, in turn, is connected to a cooling heat exchanger 321 containing heat exchange tubes 322 cooled using cooling liquid entering at 323 and exiting at 324, which, in turn, is connected to product recovery and recycle system composed of lines 325, 327, two-way valve 326, line 328, valve 329, pump 330 and line 331 and receiver 332.
In carrying out the reaction:

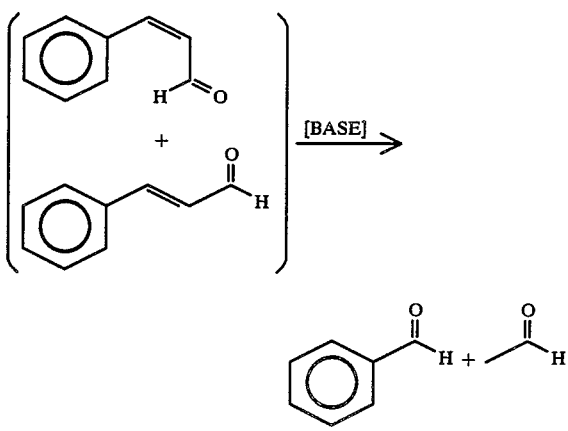

a liquid-bearing cinnamaldehyde substance, e.g., cassia oil or cinnamon oil or natural solvent-containing cassia oil or cinnamon oil 310 contained in container 309 is pumped through line 313 past valve 314 using pump 315 through line 316 into reactor 304. Simultaneously, or subsequently, base 312 such as aqueous sodium bicarbonate contained in holding tank 311 is pumped through line 317 past valve 318 using pump 319 through line 320 into reactor 304 at location 300. The resulting mixture 300 which may also contain a $C_1$–$C_5$ lower alkanol such as ethyl alcohol and/or water is heated to reflux and refluxed in packed column 305 having packing 306 (e.g., Raschig Rings or Berle Saddles) while being stirred by stirrer 303. The refluxing substance is continued to be refluxed in packed column 305 having packing 306 until analysis indicates that a desired amount of benzaldehyde and acetaldehyde has been formed in the reaction mass 300 whereupon the heat input into reactor 304 is increased whereby a significant portion of the reacting material is distilled overhead through heat exchanger 321 cooled using cooling liquid entering at 323 and exiting at 324. The resulting condensed material is passed through line 325 passed reflux valve 326 through line 328 past valve 329 using pump 330 through line 331 into receiving vessel 332. A portion of the condensed material may be refluxed back into the reactor 304 past reflux valve 326 through line 327 through pipe 308 back into the packed column 305 containing packing 306 and then back into the reactor 304. In receiver 332, the lower phase is benzaldehyde and acetaldehyde-rich (indicated by reference numeral 334) and the upper phase is solvent-rich (e.g., water and/or lower alkanol), reference numeral 333. The benzaldehyde and acetaldehyde-rich phase is then pumped into opening 338 through line 335 using pump 336 past valve 337 through line 339 into distillation column 340 at location 341 where overhead acetaldehyde-rich material is distilled through line 342 past reflux valve 343 through line 345 past valve 346 using pump 347 through line 348 into receiver 350, the acetaldehyde-rich material being indicated by reference numeral 349. The bottoms which are benzaldehyde and cinnamaldehyde-rich are removed through line 351 past return valve 352 through line 354 past valve 355 using pump 356 through line 357 into receiver 358 with the benzaldehyde/cinnamaldehyde-rich phase indicated by reference numeral 359. With regard to distillation column 340, line 344 is the reflux line for the acetaldehyde-rich phase and line 353 is the reboiler line for the benzaldehyde/cinnamaldehyde-rich phase.

The benzaldehyde/cinnamaldehyde-rich phase 359 may then be redistilled in distillation column 365 by passing the contents of receiver 358 through line 360 past valve 361 using pump 362 passed line 363 into distillation column 365 at location 364. Overhead distillate rich in benzaldehyde is then removed through line 366 past reflux valve 367 through line 370 past valve 368 using pump 369 into receiver 371, the benzaldehyde-rich material being indicated by reference numeral 372. The bottoms which are cinnamaldehyde-rich are removed through line 373 past return valve 374 through line 378 using pump 377 past valve 376 into receiver 379, the cinnamaldehyde-rich phase indicated by reference numeral 380. The bottoms return line is indicated by reference numeral 375.

The aforementiond batch apparatus is used in the practice of Example VI, infra.

FIG. 8 is the GLC profile for the reaction product of Example VI wherein the reaction:

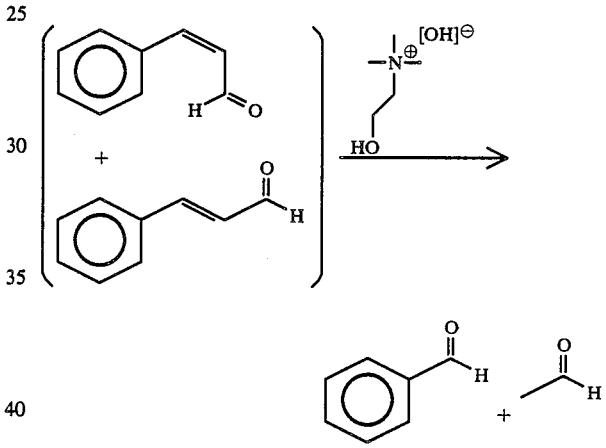

takes place. The peak indicated by reference numeral 800 is the peak for benzaldehyde. The peak indicated by reference numeral 810 is the peak for the cinnamaldehyde.

FIG. 9 is the GLC profile for a first distillation product of the reaction product of Example VI rich in benzaldehyde. The peak indicated by reference numeral 900 is the peak for benzaldehyde.

FIG. 10 is the GLC profile of a second distillation product of the reaction product of Example VI rich in benzaldehye. The peak indicated by reference numeral 101 is the peak for benzaldehyde.

FIG. 11 is the GLC profile of a third distillation product of the reaction product of Example VI rich in benzaldehyde. The peak indicated by reference numeral 111 is the peak for the benzaldehyde.

FIG. 12 is the total ion current spectrum of a GC-MS analysis of the acetaldehyde-rich material condensed in the "cold trap" 231 as indicated by reference numeral 230 on FIG. 7A. The peak indicated by reference numeral 120 is the peak for acetaldehyde. The shoulder indicated by reference numeral 121 is for ethyl alcohol. The peak indicated by reference numeral 122 is the peak for acetic acid. The peak indicated by reference numeral 123 is the peak for crotonaldehyde. The peak indicated by reference numeral 124 is the peak for benzaldehyde.

In further illustration of this invention the following examples are given. The instant invention should not be limited to these examples but is only limited by the scope of the claims as set forth, infra.

EXAMPLE I

Preparation of Natural Benzaldehyde-Cinnamaldehyde Mixture

Reaction:

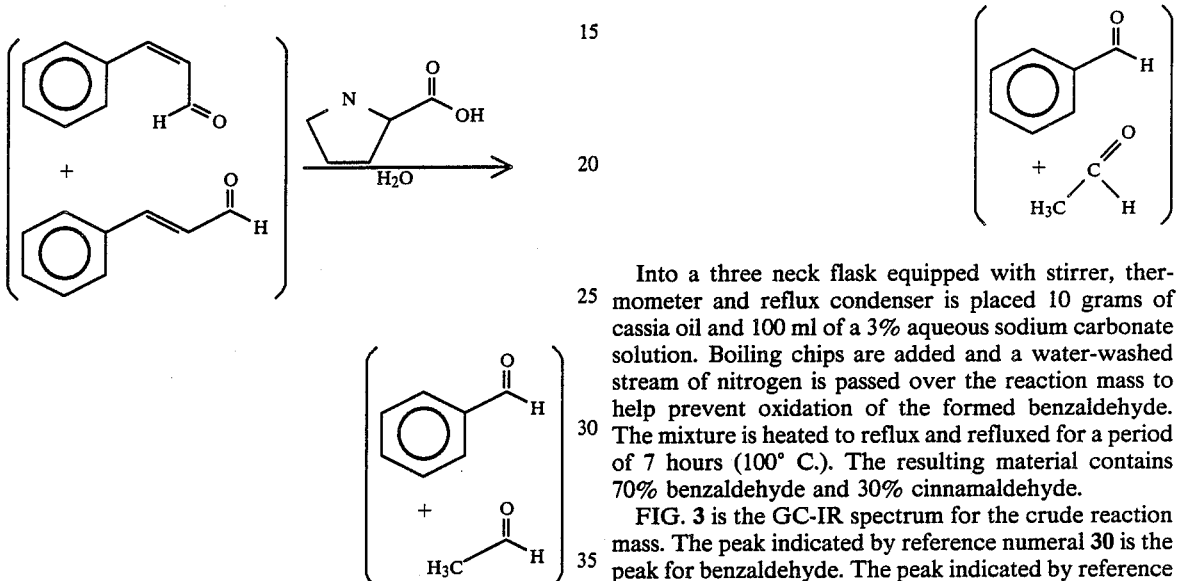

Into a 250 ml, three neck flask is placed 10 grams cassia oil, 50 ml ethanol (95% foodgrade), 50 ml distilled water and 2 grams of L-proline (natural). Boiling chips are added and a water-washed stream of nitrogen is past over the reaction mass to help prevent oxidation of the formed benzaldehyde. The mixture is heated to reflux and refluxed for a period of 18 hours at atmospheric pressure (82° C.).

The resulting product contains 40% benzaldehyde and 60% cinnamaldehyde.

FIG. 1 is the GC-IR spectrum for the resulting product. The peak indicated by reference numeral 10 is the peak for the benzaldehyde reaction product. The peak indicated by reference numeral 11 is the peak for the unreacted cinnamaldehyde.

The resulting material is fractionally distilled. The bottoms at the end of the fractional distillation are analyzed.

FIG. 2 is the GC-IR spectrum for the bottoms in the distillation pot. The peak indicated by reference numeral 20 is the peak for benzaldehyde. The peak indicated by reference numeral 21 is the peak for the cinnamaldehyde.

EXAMPLE II

Preparation of Natural Cinnamaldehyde and Natural Benzaldehyde

Reaction:

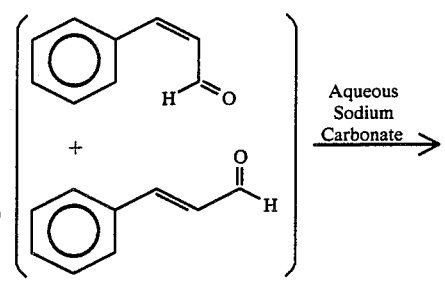

Into a three neck flask equipped with stirrer, thermometer and reflux condenser is placed 10 grams of cassia oil and 100 ml of a 3% aqueous sodium carbonate solution. Boiling chips are added and a water-washed stream of nitrogen is passed over the reaction mass to help prevent oxidation of the formed benzaldehyde. The mixture is heated to reflux and refluxed for a period of 7 hours (100° C.). The resulting material contains 70% benzaldehyde and 30% cinnamaldehyde.

FIG. 3 is the GC-IR spectrum for the crude reaction mass. The peak indicated by reference numeral 30 is the peak for benzaldehyde. The peak indicated by reference numeral 31 is the peak for the cinnamaldehyde. (Conditions: Carbowax column programmed at 75°–225° C. at 3° C. per minute).

EXAMPLE III

At the rate of 3% to two separate samples of natural cherry liquer the product of Example I and the product of Example II are added. In each of the cases the resulting cherry liqueur has a more natural, more aesthetically pleasing rich, ripe cherry aroma and taste nuance remeniscent of natural cherry flavor. A bench panel of five members not associated with the inventive entity of the instant application unanimously prefers the cherry liquer containing the products of Examples I and II to the products not containing such materials.

EXAMPLE IV

Each of the cherry liqueurs produced in Example III is intimately admixed with carbonated Perrier ® water at the weight ratios of 50:50 (Perrier ® water:cherry liquer). The resulting "carbonated" beverage has an excellent, natural cherry aroma and taste. A bench panel of five members prefers the "resulting cherry soda" to a similar cherry soda produced without the use of the products of Examples I or II.

EXAMPLE V

A cherry fruit puree is produced (for the purpose of adding to an unflavored yogurt). At the level of 0.1%, each of the products of Examples I and II is added to separate samples of the cherry puree. At the rate of 10% each of the cherry puree samples is added to unflavored yogurt and intimately admixed therewith. A bench panel of five members not associated with the inventive entity of the instant application unanimously prefers the cherry flavored yogurt containing the products of Examples I and II to the same product not containing such materials.

EXAMPLE VI

Preparation of Natural Benzaldehyde-Cinnamaldehyde Mixture and Natural Acetaldehyde Composition Reaction:

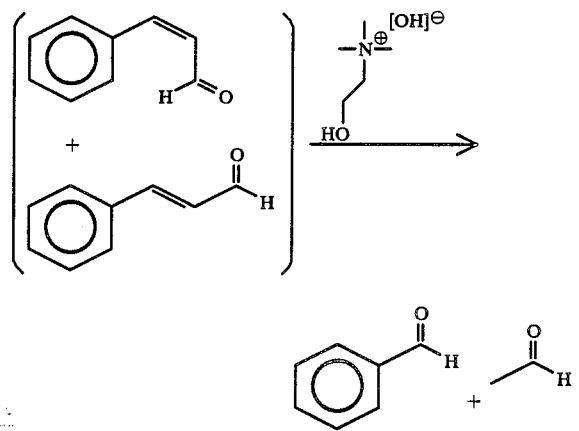

Into a reaction vessel in the apparatus as set forth in FIG. 7A, equipped with stirrer, thermometer and reflux packed column fitted with overhead condenser to which are connected receivers for benzaldehyde-rich materials and acetaldehyde-rich materials as specified, supra, are placed 1 liter of water, 50 grams cassia oil and 20 ml of a 45% solution of choline base in methyl alcohol.

The reaction mass is heated to reflux and maintained at reflux for a period of 0.5 hours, at which point in time, 20 ml of a 45% solution of choline base in methanol is added. The reaction mass is continued to be refluxed for a period of 4 hours, slowly removing the methanol from the system through the overhead condenser with the reflux temperature rising from 65° to 99° C. At the end of the 4 hour period, 300 ml water is added to the reaction mass. Ther eaction mass is then refluxed for a period of 8 hours. At the end of the 8 hour refluxing period, additional heat is imparted to the reaction vessel whereby the reaction product begins to be distilled using the overhead condenser 199 and the controlled reaction product recovery apparatus shown in FIGS. 7A and 7B into (i) receiver 218 where the benzaldehyde-rich fraction 220 is collected and (ii) cold trap 231 where the acetaldehyde-rich material 230 is condensed and collected.

The original cassia oil utilized contained 88% cinnamaldehyde.

The yield of benzaldehyde based on 88% cinnamaldehyde-containing cassia oil is 65%. The third distillation fraction contained a ratio of benzaldehyde:-cinnamaldehyde of 13:1.

FIG. 8 is the GLC profile of the reaction product prior to the first distillation. The peak indicated by reference numeral 800 is the peak for benzaldehyde. The peak indicated by reference numeral 810 is the peak for cinnamaldehyde.

FIG. 9 is the GLC profile for the first distillation of the benzaldehyde-rich phase 89. The peak indicated by reference numeral 900 is the peak for benzaldehyde.

FIG. 10 is the GLC profile for the second distillation of the lower phase benzaldehyde-rich product. The peak indicated by reference numeral 101 is the peak for benzaldehyde.

FIG. 11 is the GLC profile for the third distillation of the benzaldehyde-rich phase. The peak indicated by reference numeral 111 is the peak for benzaldehyde.

FIG. 12 is the total ion current spectrum of a GC-MS analysis of the acetaldehyde-rich composition containing minor impurities 230 trapped in cold trap 231 of the apparatus of FIG 7A. The peak indicated by reference numeral 120 is the peak for the acetaldehyde. The shoulder indicated by reference numeral 121 is for ethyl alcohol. The peak indicated by reference numeral 122 is the peak for acetic acid. The peak indicated by reference numeral 123 is the peak for croton-aldehyde. The peak indicated by reference numeral 124 is the peak for benzaldehyde.

EXAMPLE VII

The following sweet cherry flavor formulation is prepared:

| Ingredients | Parts by Weight |
|---|---|
| Allyl isovalerate | 15.0 |
| Amyl butyrate | 200.0 |
| Anisic aldehyde | 37.0 |
| Anisyl acetate | 25.0 |
| Anisyl butyrate | 12.0 |
| Anisyl propionate | 12.0 |
| Benzyl acetate | 50.0 |
| Third distillation product of the reaction product of Example VI (identified by the GLC profile of FIG. 11) | 4,658.0 |
| Eugenol | 7.0 |
| Cyclohexyl cinnamate | 5.0 |
| Cyclohexyl formate | 8.0 |
| Ethyl acetate | 680.0 |
| Ethyl butyrate | 152.0 |
| Ethyl methylglycidate | 100.0 |
| Rhodinol | 60.0 |
| Beta-ionone | 4.0 |
| Jasmine absolute | 13.0 |
| Citral | 1.0 |
| Maltol (5% in ethanol) | 1.0 |
| Orris butter | 30.0 |
| Orris resinoid | 160.0 |
| Rhodinyl formate | 1.0 |
| Rhodinyl isovalerate | 12.0 |
| Para-Toluic aldehyde | 500.0 |
| Vanillin | 400.0 |
| Propylene glycol | 2,920.0 |
| Total | 10,000.0 |

The resulting flavor is compared with the same flavor produced using a mixture of bitter almond essential oil and extracted ceylon, cinnamon, cinnamaldehyde in a combined amount of 4658.0. The cherry flavor containing the third distillation product of the reaction product of Example VI is unanimously preferred by a bench panel of five members independent of the inventive entity due to the more natural nature of the overall flavor. The natural cherry nuances imparted using the third distillation product of the reaction product of Example VI give rise to unexpected, unobvious and advantageous properties of the resulting cherry flavor formulation.

EXAMPLE VIII

A. Powder Flavor Formulation

Twenty grams of the flavor composition of Example VII is emulsified in a solution containing 300 grams gum acacia and 700 grams of water. The emulsion is spray dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredients | Parts by Weight |
| --- | --- |
| Liquid cherry flavor composition of Example VII | 20 |
| Propylene glycol | 9 |
| Cab-O-Sil ® M-5 (brand of silica produced by the Cabot Corp. of 125 High Street, Boston, Mass. 02110) | 5 |
| Physical properties | |
| Surface area | 200 m$^2$/gm |
| Nominal particle size | 0.012 microns |
| Density | 2.3 lbs/cu. ft. |

The Cab-O-Sil ® is dispersed in the liquid cherry flavor composition of Example VII with vigorous stirring thereby resulting in a viscous liquid. Seventy-one parts by weight of the powder flavor composition of Part A, supra, is then blended into said viscous liquid with stirring at 25° C. for a period of 30 minutes resulting in a dry, free-flowing sustained release flavor powder.

EXAMPLE IX

Ten parts by weight of 50 Bloom pigskin gelatin is added to ninety parts by weight of water at a temperature of 150° F. The mixture is agitated until the gelatin is completely dissolved and the solution is cooled to 120° F. Twenty parts by weight of the liquid flavor composition of Example VII is added to the solution which is then homogenized to form an emulsion having a particle size typically in the range of 5–40 microns. The material is kept at 120° F. under which conditions the gelatin will not gel.

Coacervation is induced by adding slowly and uniformly, forty parts by weight of a 20% aqueous solution of sodium sulphate. During coacervation of gelatin, molecules are deposited uniformly about each oil droplet as a nucleus.

Gelation is effected by pouring the heated coacervate mixture into 1,000 parts by weight of a 7% aqueous solution of sodium sulphate at 65° F. The resulting gelled coacervate may be filtered and washed with water at temperatures below the melting point of gelation, to remove the salt.

Hardening of the filter cake, in this example, is effected by washing with 200 parts by weight of 37% solution of formaldehyde in water. The cake is then washed to remove the residual formaldehyde.

EXAMPLE X

Chewing Gum

One hundred parts by weight of chicle are mixed with four parts by weight of the flavor prepared in accordance with Example VIII, Part B. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting natural cherry flavor.

EXAMPLE XI

One hundred parts by weight of chicle are mixed with eighteen parts by weight of the flavor prepared in accordance with Example IX. Three hundred parts of sucrose and one hundred parts of corn syrup are then added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of 3" each. On chewing, the chewing gum has a pleasant, long-lasting natural cherry flavor.

EXAMPLE XII

Toothpaste Formulation

The following separate groups of ingredients are prepared:

| Parts by Weight | Ingredients |
| --- | --- |
| Group "A" | |
| 30.200 | Glycerine |
| 15.325 | Distilled water |
| 0.100 | Sodium benzoate |
| 0.125 | Saccharin sodium |
| 0.400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example VIII, Part B |
| 100.000 | (Total) |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure, yields a pleasant, sweet, cherry flavor of constant strong intensity throughout said procedure (1–1.5 minutes).

EXAMPLE XIII

Chewable Vitamin Tablets

The flavor material produced according to the process of Example VIII, Part B, is added to a chewable vitamin tablet formulation at a rate of 10 gm/kg which chewable vitamin tablet formulation is prepared as follows:

In a Hobart Mixer, the following materials are blended to homogeneity:

| Ingredients | Gms/1000 Tablets |
|---|---|
| Vitamin C (ascorbic acid as ascorbic acid-sodium ascorbate mixture 1:1) | 70.000 |
| Vitamin $B_1$ (thiamine mononitrate) as Rocoat ® thiamine mononitrate 33⅓% (Hoffman LaRoche) | 4.000 |
| Vitamin $B_2$ (riboflavin) as Rocoat ® riboflavin 33⅓% | 5.000 |
| Vitamin $B_6$ (pyridoxine hydrochloride) as Rocoat ® pyridoxine hydrochloride 33⅓% | 4.000 |
| Niacinamdie as Rocoat ® niacinamide 33⅓% | 33.000 |
| Calcium pantothenate | 11.000 |
| Vitamin $B_{12}$ (cyanocobalamin) as Merck 0.1% in gelatin | 3.500 |
| Vitamin E (dl-alpha topcopheryl acetate) as dry Vitamin E acetate 33⅓% Roache | 6.600 |
| d-Biotin | 0.044 |
| Certified lake color | 5.000 |
| Flavor of Example VIII, Part B | as indicated above |
| Sweetener sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, longlasting, consistently strong, cherry flavor for a period of 12 minutes.

EXAMPLE XIV

Chewing Tobacco

Onto 100 pounds of tobacco for chewing (85% Wisconsin lead and 15% Pennsylvania lead) the following casing is sprayed at a rate of 30%:

| Ingredients | Parts by Weight |
|---|---|
| Corn syrup | 60.0 |
| Licorice | 10.0 |
| Glycerine | 20.0 |
| Fig juice | 4.6 |
| Prune juice | 5.0 |
| Flavor material of Example VIII of Part B | 0.4 |

The resultant product is redried to a moisture content of 20%. On chewing, this tobacco has an excellent substantially consistent, long-lasting, sweet, cherry nuance (20 minutes) in conjunction with the main fruity tobacco note.

EXAMPLE XV

Flavored Foodstuff 2.25 Ounces of a coconut macaroon mix distributed by Drake Bakeries, Division of Borden, Inc. of Columbus, Ohio 43215 is intimately admixed at the level of 20 ppm with the benzaldeyde/cinnamaldehyde mixture (second distillation product) prepared according to Example VI.

The coconut macaroon composition contains corn syrup, coconut, sugar and egg whites.

The coconut macaroon composition is then baked at 325° F. at atmospheric pressure for a period of 20 minutes. The resultant coconut macaroon cookies have an excellent "natural coconut" notes with intense almond nuances not present in the cookies without the composition of Example VI.

When the composition of Example VI is replaced with the compositions of Examples I or II, a similar natural coconut almond nuance is created.

EXAMPLE XVI

Tobacco Flavor Formulation and Tobacco

A tobacco mixture is produced by admixing the following materials:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tabacco:

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

EXAMPLE XVII

Apple Flavor Formulation

The following basic apple flavor formulation is prepared:

| Ingredients | Parts by Weight |
|---|---|
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95%-food grade ethanol | 100.0 |

This basic apple flavor is compared, in water, with and without the addition of natural acetaldehyde prepared according to Example VI at the rate of 6 ppm and at the rate of 10 ppm in water. The flavor with the addition of the natural acetaldehyde composition has a fresh apple juice character with light fruity topnotes. Both notes are missing in the flavor that does not contain the natural acetaldehyde composition of Example VI. For this reason, the flavor with the natural acetaldehyde composition of Example VI is preferred unanimously by a three-member bench panel.

EXAMPLE XVIII

A. Powder Flavor Formulation

20 Grams of the flavor formulation of Example IV is emulsified in a solution containing 300 g gum acacia and 700 g water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| Liquid Apple Flavor of Example IV | 20.00 |
| Propylene Glycol | 9.00 |
| Cab-O-Sil ® M-5 Brand of Silica produced by the Cabot Corporation of 125 High Street, Boston, Mass. 02110; Physical Properties | 5.00 |
| Surface Area | 200 m²/gm |
| Nominal particle size | 0.012 microns |
| Density | 2.3 lbs/cu. ft.) |

The Cab-O-Sil is dispersed in the liquid apple flavor composition of Example XVII with vigorous stirring, thereby resulting in a viscous liquid. 71 Parts by weight of the powder flavor composition of Part 1, supra, is then blended into the said viscous liquid, with stirring at 25° C. for a period of 30 minutes, resulting in a dry, free flowing sustained release powder.

EXAMPLE XIX 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid apple flavor composition of Example XVII is added to the solution which is then homogenized to form an emulsion having particle size typically in the range of 5–40 microns. This material is kept at 120° F. under which conditions, the gelatin will not jell.

Coacervation is induced by adding slowly and uniformly, 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XX

Chewing Gum 100 parts by weight of chicle are mixed with 4 parts by weight of the flavor prepared in accordance with Example XVIII(V). 300 Parts of sucrose and 100 parts of corn syrup are added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting apple flavor.

EXAMPLE XXI

Chewing Gum

100 Parts by weight of chicle are mixed with 18 parts by weight of the flavor prepared in accordance with Example XIX. 300 Parts of sucrose and 100 parts of corn syrup are then added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting apple flavor.

EXAMPLE XXII

Toothpaste Formulation

The following separate groups of ingredients are prepared:

| Parts by Weight | Ingredient |
|---|---|
| | Group "A" |
| 30.200 | Glycerine |
| 15.325 | Distilled Water |
| .100 | Sodium Benzoate |
| .125 | Saccharin Sodium |
| .400 | Stannous Fluoride |
| | Group "B" |
| 12.500 | Calcium Carbonate |
| 37.200 | Dicalcium Phosphate (Dihydrate) |
| | Group "C" |
| 2.000 | Sodium N—Lauroyl Sarcosinate (foaming agent) |
| | Group "D" |
| 1.200 | Flavor Material of Example XVIII(B) |
| 100.00 | - TOTAL |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium-n-lauroyl sarcosinate.
5. The resultant slurry is then blended for one hour. The completed paste is then transferred to a three roller mill and then homogenized, and finally tubes.

The resulting toothpaste, when used in a normal toothbrushing procedure yields a pleasant apple flavor, of constant strong intensity throughout said procedure (1-1.5 minutes).

EXAMPLE XXIII

Chewable Vitamin Tablets

The flavor material produced according to the process of Example XVIII(B) is added to a Chewable Vitamin Tablet Formulation at a rate of 10 gm/Kg, which Chewable Vitamin Tablet Formulation is prepared as follows:

In a Hobart Mixer, the following materials are blended to homogeneity:

| Ingredients | Gms/1000 Tablets |
| --- | --- |
| Vitamin C (ascorbid acid) as ascorbic acid-sodium ascorbate mixture 1:1 | 70.11 |
| Vitamin B$_1$ (thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example XVIII(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, longlasting, consistently strong apple flavor for a period of 12 minutes.

What is claimed is:

1. A method of making benzaldehyde comprising:
   (i) dispersing cinnamaldehyde in water:
   (ii) converting the cinnamaldehyde to benzaldehyde according to the reaction:

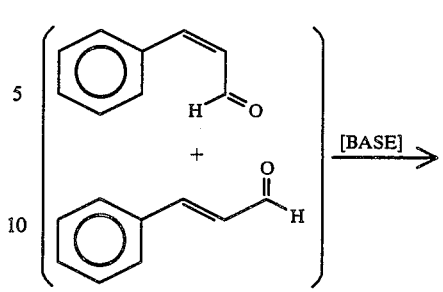

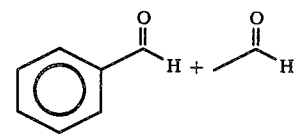

under the action of heat at reflux conditions in the presence of a mixture of natural base and in the presence of an ionic surfactant which is lecithin having the structure:

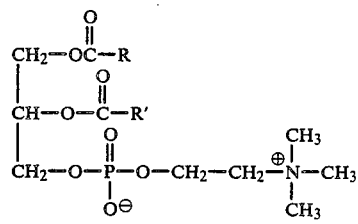

wherein the residues:

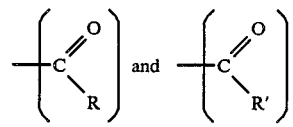

represent palmitoyl, stearoyl, oleyl, linoleyl, linolenyl and $C_{20}$-$C_{22}$ acid residues, the temperature range of the reaction being between 40° C. and 150° C.; the pressure range of the reaction being between 0.2 and 10 atmospheres; the time of reaction being between 5 and 80 hours; the mole ratio of base:cinnamaldehyde being from 0.1:1 up to 4:1;
   (iii) distilling benzaldehyde and acetaldehyde from the cinnamaldehyde; and
   (iv) recovering benzaldehyde from the distillate.

* * * * *